(12) United States Patent
Matsuda et al.

(10) Patent No.: US 8,658,770 B2
(45) Date of Patent: Feb. 25, 2014

(54) INTEGRIN ALPHA 8-BETA 1-SPECIFIC MONOCLONAL ANTIBODY

(75) Inventors: Haruo Matsuda, Higashi-Hiroshima (JP); Norihisa Nishimichi, Higashi-Hiroshima (JP); Yoshiko Tateishi, Higashi-Hiroshima (JP); Yasuyuki Yokosaki, Hiroshima (JP)

(73) Assignee: Hiroshima University, Higashi-Hiroshima-shi (JP)

( * ) Notice: Subject to any disclaimer, the term of this patent is extended or adjusted under 35 U.S.C. 154(b) by 0 days.

(21) Appl. No.: 13/503,332

(22) PCT Filed: Oct. 19, 2010

(86) PCT No.: PCT/JP2010/068374
§ 371 (c)(1),
(2), (4) Date: Apr. 20, 2012

(87) PCT Pub. No.: WO2011/049082
PCT Pub. Date: Apr. 28, 2011

(65) Prior Publication Data
US 2012/0237530 A1 Sep. 20, 2012

(30) Foreign Application Priority Data

Oct. 21, 2009 (JP) ................................ 2009-242891
Apr. 1, 2010 (JP) ................................ 2010-085473

(51) Int. Cl.
*C07K 16/00* (2006.01)
*C07K 16/46* (2006.01)
*C07K 16/28* (2006.01)
(52) U.S. Cl.
USPC .................. 530/387.1; 530/387.3; 530/387.9; 530/388.22
(58) Field of Classification Search
None
See application file for complete search history.

(56) References Cited

U.S. PATENT DOCUMENTS

| | | | | |
|---|---|---|---|---|
| 5,654,403 | A | * | 8/1997 | Smith et al. ............... 530/387.3 |
| 5,859,205 | A | * | 1/1999 | Adair et al. ................ 530/387.3 |
| 6,303,766 | B1 | * | 10/2001 | Grabau et al. ............... 536/23.1 |
| 2007/0003551 | A1 | | 1/2007 | Lindsay |

FOREIGN PATENT DOCUMENTS

| | | |
|---|---|---|
| JP | 2007-527201 A | 9/2007 |
| JP | 2008-510008 A | 4/2008 |
| WO | 2004/069875 A2 | 8/2004 |
| WO | 2006/023420 A2 | 3/2006 |

OTHER PUBLICATIONS

Schnapp et al. Sequence and tissue distribution of the human integrin alpha 8 subunit: a beta 1-associated alpha subunit expressed in smooth muscle cells.. Journal of Cell Science 108, 537-544 (1995).*

Denda et al. Utilization of a Soluble Integrin-Alkaline Phosphatase Chimera to Characterize Integrin α8β1 Receptor Interactions with Tenascin: Murine α8β1 Binds to the RGD Site in Tenascin-C Fragments, but Not to Native Tenascin-C. Biochemistry. Apr. 21, 1998;37(16):5464-74.*

Varnum-Finney et al. The integrin receptor alpha 8 beta 1 mediates interactions of embryonic chick motor and sensory neurons with tenascin-C. Neuron. Jun. 1995;14(6):1213-22.*

Campbell A, General properties and applications of monoclonal antibodies, Elsevier Science Publishers, section 1.1, pp. 1-32, 1984.*

Klimka et al., Human anti-CD30 recombinant antibodies by guided phage antibody selection using cell panning. British Journal of Cancer (2000) 83:252-260.*

Beiboer et al.,Guided selection of a pan carcinoma specific antibody reveals similar binding characteristics yet structural divergence between the original murine antibody and its human equivalent. J. Mol., Biol. (2000) 296:833-849.*

Eduardo Padlan, Anatomy of the antibody molecule. Mol Immunol. Feb. 1994;31(3):169-217.*

Brown et al. Tolerance of single, but not multiple, amino acid replacements in antibody VH CDR 2: a means of minimizing B cell wastage from somatic hypermutation? J. Immuno. May 1996, 3285-91.*

Paul, Fundamental Immunology, 3rd Edition, 1993, pp. 292-295.*

Rudikoff et al Single amino acid substitution altering antigen-binding specificity. Proc Natl Acad Sci U S A. Mar. 1982;79(6): 1979-83.*

Vajdos FF, et al., "Comprehensive functional maps of the antigen-binding site of an anti-ErbB2 antibody obtained with shotgun scanning mutagenesis," J Mol Biol. Jul. 5, 2002;320(2):415-28.*

Amended Claims submitted Jun. 6, 2011, in PCT/JP2010/068374, filed Oct. 19, 2010, which is a national stage of the present application, 11 pages.

International Preliminary Report on Patentability, mailed Jul. 19, 2011, issued in corresponding International Application No. PCT/JP20101068374, filed Oct. 19, 2010, 16 page.

Written Reply mailed Nov. 16, 2010, submitted in corresponding International Application No. PCT/JP2010/068374, filed Oct. 19, 2010, 16 pages.

Farias, E., et al., "Integrin α8β1-Fibronectin Interactions Promote Cell Survival via PI3 Kinase Pathway," Biochemical and Biophysical Research Communications 329:305-311, 2005.

International Search Report mailed Nov. 16, 2010, issued in corresponding International Application No. PCT/JP2010/068374, filed Oct. 19, 2010, 4 pages.

Levine, D., et al., "Expression of the Integrin α8β1 During Pulmonary and Hepatic Fibrosis," American Journal of Pathology 156(6):1927-1935, Jun. 2000.

(Continued)

*Primary Examiner* — Maher Haddad
(74) *Attorney, Agent, or Firm* — Christensen O'Connor Johnson Kindness PLLC

(57) ABSTRACT

[Object] To obtain an anti-integrin α8β1 antibody which binds to integrin α8β1 derived from mammals of different species. Also, to obtain an anti-integrin α8β1 antibody which inhibits binding between integrin α8β1 and its ligand.

[Solution] Anti-integrin α8β1 antibodies which bind to integrin α8β1 derived from mammals of different species have been obtained. In addition, inhibitors, which contain an anti-integrin α8β1 antibody, of binding between integrin α8β1 and its ligand have been obtained.

8 Claims, 6 Drawing Sheets

(56) References Cited

OTHER PUBLICATIONS

Müller, U., et al., "Integrin α8β1 is Critically Important for Epithelial-Mesenchymal Interactions During Kidney Morphogenesis," Cell 88(5):603-613, Mar. 1997.

Nagata, M., and Shinsuke Tomari, "Nephron Keisei no Bunshi Seigyo", Kidney and Dialysis 51(5):569-577, 2001.

Nakamura, N., et al., "Establishment of a Chicken Monoclonal Antibody Panel Against Mammalian Prion Protein," The Journal of Veterinary Medical Science 66(7):807-814, 2004.

Nakamura, N., et al., "Two Expression Vectors for the Phage-Displayed Chicken Monoclonal Antibody," Journal of Immunological Methods 280:157-164, 2003.

Nishimichi, N., et al., "Generation of Chicken Monoclonal Antibodies Against Mouse Osteopontin and Their Application," Poster, Journal of Japanese Biochemical Society, Shoroku CD, #4P-0509.

Sato, Y., et al., "Molecular Basis of the Recognition of Nephronectin by Integrin α8β1," The Journal of Biological Chemistry 284(21): 14524-14536, May 2009.

Schnapp, L.M., et al., "The Human Integrin α8β1 Functions as a Receptor for Tenascin, Fibronectin, and Vitronectin," The Journal of Biological Chemistry 270(39):23196-23202, Sep. 1995.

Siva, A.C., et al., "Selection of Anti-Cancer Antibodies from Combinatorial Libraries by Whole-Cell Panning and Stringent Subtraction with Human Blood Cells," Journal of Immunological Methods 330:109-119, 2008.

Stüve, O., et al., "α4-Integrin Antagonism With Natalizumab, Effects and Adverse Effects," Journal of Neurology 255 (Suppl 6):58-65, Dec. 2008.

* cited by examiner

SEQUENCE LISTING

<160> NUMBER OF SEQ ID NOS: 24

<210> SEQ ID NO 1
<211> LENGTH: 5
<212> TYPE: PRT
<213> ORGANISM: chicken

<400> SEQUENCE: 1

Ser Tyr Asp Met Val
1               5

<210> SEQ ID NO 2
<211> LENGTH: 16
<212> TYPE: PRT
<213> ORGANISM: chicken

<400> SEQUENCE: 2

Ile Tyr Ser Ala Gly Ser Gly Pro Gln Tyr Ala Pro Ala Val Lys Gly
1               5                   10                  15

<210> SEQ ID NO 3
<211> LENGTH: 18
<212> TYPE: PRT
<213> ORGANISM: chicken

<400> SEQUENCE: 3

Ala Asp Ser Thr Tyr Cys Ala Ser Gly Ser Cys Tyr Ala Ala Asp Ser
1               5                   10                  15

Ile Asp

<210> SEQ ID NO 4
<211> LENGTH: 5
<212> TYPE: PRT
<213> ORGANISM: chicken

<400> SEQUENCE: 4

Ser Tyr Asp Met Ala
1               5

<210> SEQ ID NO 5
<211> LENGTH: 16
<212> TYPE: PRT
<213> ORGANISM: chicken

<400> SEQUENCE: 5

Ile Asp Asp Asp Asp Ser Phe Thr Leu Tyr Gly Ala Ala Val Lys Gly
1               5                   10                  15

<210> SEQ ID NO 6
<211> LENGTH: 16
<212> TYPE: PRT
<213> ORGANISM: chicken

<400> SEQUENCE: 6

Val Gly Asp Gly Tyr Cys Gly Trp Ser Ala Cys Gly Gly Ser Ile Asp
1               5                   10                  15

<210> SEQ ID NO 7
<211> LENGTH: 5
<212> TYPE: PRT
<213> ORGANISM: chicken

```
<400> SEQUENCE: 7

Gly His Asp Met Ala
1               5

<210> SEQ ID NO 8
<211> LENGTH: 16
<212> TYPE: PRT
<213> ORGANISM: chicken

<400> SEQUENCE: 8

Ile Gly Ser Ser Gly Ser Asn Thr Asn Tyr Gly Thr Ala Val Lys Gly
1               5                   10                  15

<210> SEQ ID NO 9
<211> LENGTH: 15
<212> TYPE: PRT
<213> ORGANISM: chicken

<400> SEQUENCE: 9

Pro Gly Ser Cys Tyr Gly Cys Thr Pro Asp Ala Gly Glu Ile Asp
1               5                   10                  15

<210> SEQ ID NO 10
<211> LENGTH: 8
<212> TYPE: PRT
<213> ORGANISM: chicken

<400> SEQUENCE: 10

Ser Gly Gly Gly Ser Trp Tyr Gly
1               5

<210> SEQ ID NO 11
<211> LENGTH: 7
<212> TYPE: PRT
<213> ORGANISM: chicken

<400> SEQUENCE: 11

Asp Asn Thr Asn Arg Pro Ser
1               5

<210> SEQ ID NO 12
<211> LENGTH: 9
<212> TYPE: PRT
<213> ORGANISM: chicken

<400> SEQUENCE: 12

Gly Ser Ala Asp Ser Thr Asp Ala Val
1               5

<210> SEQ ID NO 13
<211> LENGTH: 8
<212> TYPE: PRT
<213> ORGANISM: chicken

<400> SEQUENCE: 13

Ser Gly Asp Glu Ser Tyr Tyr Gly
1               5

<210> SEQ ID NO 14
<211> LENGTH: 7
<212> TYPE: PRT
<213> ORGANISM: chicken
```

```
<400> SEQUENCE: 14

Ser Asn Asp Lys Arg Pro Ser
1               5

<210> SEQ ID NO 15
<211> LENGTH: 11
<212> TYPE: PRT
<213> ORGANISM: chicken
<220> FEATURE:
<221> NAME/KEY: UNSURE
<222> LOCATION: (2)..(2)
<223> OTHER INFORMATION: Unsure about the sequence assignment

<400> SEQUENCE: 15

Gly Xaa Tyr Asp Ser Ser Thr Tyr Ala Gly Ile
1               5                   10

<210> SEQ ID NO 16
<211> LENGTH: 9
<212> TYPE: PRT
<213> ORGANISM: chicken

<400> SEQUENCE: 16

Ser Gly Ser Ser Gly Ser Tyr Tyr Gly
1               5

<210> SEQ ID NO 17
<211> LENGTH: 7
<212> TYPE: PRT
<213> ORGANISM: chicken

<400> SEQUENCE: 17

Glu Ser Thr Lys Arg Pro Ser
1               5

<210> SEQ ID NO 18
<211> LENGTH: 10
<212> TYPE: PRT
<213> ORGANISM: chicken

<400> SEQUENCE: 18

Gly Asn Glu Asp Ser Ser Tyr Val Gly Ile
1               5                   10

<210> SEQ ID NO 19
<211> LENGTH: 5
<212> TYPE: PRT
<213> ORGANISM: chicken
<220> FEATURE:
<221> NAME/KEY: misc_feature
<222> LOCATION: (1)..(2)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be any naturally occurring amino acid

<400> SEQUENCE: 19

Xaa Xaa Asp Met Xaa
1               5

<210> SEQ ID NO 20
<211> LENGTH: 16
<212> TYPE: PRT
<213> ORGANISM: chicken
```

```
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid

<400> SEQUENCE: 20

Ile Xaa Xaa Xaa Xaa Ser Xaa Xaa Xaa Tyr Xaa Xaa Ala Val Lys Gly
1               5                   10                  15

<210> SEQ ID NO 21
<211> LENGTH: 18
<212> TYPE: PRT
<213> ORGANISM: chicken
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(8)
<223> OTHER INFORMATION: Xaa can be any naturally occurring amino acid
<220> FEATURE:
<221> NAME/KEY: misc_feature
<222> LOCATION: (10)..(16)
<223> OTHER INFORMATION: Xaa can be any naturally occurring amino acid

<400> SEQUENCE: 21

Xaa Xaa Xaa Xaa Tyr Xaa Xaa Xaa Gly Xaa Xaa Xaa Xaa Xaa Xaa Xaa
1               5                   10                  15

Ile Asp

<210> SEQ ID NO 22
<211> LENGTH: 9
<212> TYPE: PRT
<213> ORGANISM: chicken
<220> FEATURE:
<221> NAME/KEY: misc_feature
<222> LOCATION: (3)..(5)
<223> OTHER INFORMATION: Xaa can be any naturally occurring amino acid
<220> FEATURE:
<221> NAME/KEY: misc_feature
<222> LOCATION: (7)..(7)
<223> OTHER INFORMATION: Xaa can be any naturally occurring amino acid

<400> SEQUENCE: 22

Ser Gly Xaa Xaa Xaa Ser Xaa Tyr Gly
1               5

<210> SEQ ID NO 23
<211> LENGTH: 7
<212> TYPE: PRT
<213> ORGANISM: chicken
<220> FEATURE:
<221> NAME/KEY: misc_feature
<222> LOCATION: (1)..(4)
<223> OTHER INFORMATION: Xaa can be any naturally occurring amino acid

<400> SEQUENCE: 23

Xaa Xaa Xaa Xaa Arg Pro Ser
1               5
```

-continued

```
<210> SEQ ID NO 24
<211> LENGTH: 12
<212> TYPE: PRT
<213> ORGANISM: chicken
<220> FEATURE:
<221> NAME/KEY: misc_feature
<222> LOCATION: (2)..(12)
<223> OTHER INFORMATION: Xaa can be any naturally occurring amino acid

<400> SEQUENCE: 24

Gly Xaa Xaa Xaa Xaa Xaa Xaa Xaa Xaa Xaa Xaa Xaa
1               5                   10
```

INTEGRIN ALPHA 8-BETA 1-SPECIFIC MONOCLONAL ANTIBODY

STATEMENT REGARDING SEQUENCE LISTING

The sequence listing associated with this application is provided in text format in lieu of a paper copy and is hereby incorporated by reference into the specification. The name of the text file containing the sequence listing is 39209_Sequence_Listing_Final_2012-04-16.txt. The text file is 3.23 KB; was created on Apr. 16, 2012, and is being submitted via EFS-Web with the filing of the specification.

TECHNICAL FIELD

The present invention relates to anti-integrin α8β1 antibodies, and to a process for producing the same.

BACKGROUND ART

Integrins are expressed on a cell membrane, and constitute a single-transmembrane heterodimeric adhesion molecule. It has been known to have 24 kinds of integrins including 18 types of α chain and 8 types of β chain. By binding to its ligand, the recognized integrin transmits various signals to the inside of a cell, and regulates a variety of cellular biological phenomena such as cell morphogenesis, proliferation, and migration of leukocytes at the sites of inflammation.

In addition, the integrin α8 chain forms a heterodimer with the β1 chain to be the integrin α8β1. This integrin recognizes RGD stites in extracellular matrix proteins such as fibronectin, vitronectin, tenascin, and osteopontin. The integrin α8 chain is expressed on mesangial cells in a kidney, vascular smooth muscle cells, fibroblasts, or the like. It has been reported in an experiment using knockout mice that the integrin α8 chain is among the most critical integrins during kidney morphogenesis (Non-Patent Document 1). Also, a correlation with a disease is reported, including that the integrin α8 chain is expressed in re-stenotic artery in rats after vascular injury or in lungs of mice with pulmonary fibrosis (Non-Patent Document 2). Detailed physiological functions of this integrin remain unresolved.

Meanwhile, recently, research and development on an antibody medicine and an antibody diagnostic agent has been progressing. Monoclonal antibodies against integrins have been researched on applications to a therapeutic or diagnostic agent for a disease involving the integrins. For example, Natalizumab, a blocking monoclonal antibody which binds to integrin α4β1, having a multiple sclerosis indication (Non-Patent Document 3) has been listed on the market. It has been reported that Vedolizumab exerts a therapeutic effect on inflammatory bowel disease.

As to an anti-integrin α8β1 antibody (hereinafter, may be referred to as an "integrin α8β1-binding antibody"), an antibody which can be used to detect the integrin by Western blotting and an antibody which can be used to detect the integrin by flow cytometry analysis have been described in Non-Patent Document 4.

Patent Document 1 discloses an Fc variant of an antibody which binds to integrin αVβ3. In addition, an embodiment of Patent Document 1 includes integrin α8β1 as a candidate for an integrin binding to the Fc variant.

Patent Document 2 discloses a recombinant human immunoglobulin having an antigen-binding region containing a particular amino acid sequence. Also, the Claims of Patent Document 2 includes integrin α8β1 as an antigen candidate.

PRIOR ART REFERENCE

Patent Document

Patent Document 1: JP2008-510008A
Patent Document 2: JP2007-527201A

Non Patent Literature

Non-Patent Document 1: Muller et al., Cell, 1997, Mar. 7, 88(5), 603-13.
Non-Patent Document 2: Levine et al., Am J Pathol., 2000, June, 156(6), 1927-35.
Non-Patent Document 3: Stuve et al., J Neurol., 2008, December, 255, Suppl 6, 58-65.
Non-Patent Document 4: Sato et al., J Biol Chem., 2009, May 22, 284(21), 14524-36 (Epub: Apr. 2, 2009).

SUMMARY OF THE INVENTION

Problems to be Solved by the Invention

Unfortunately, the conventional techniques as described in the above documents have had room for improvement regarding the following points. Non-Patent Documents 1 and 2 describe that expression of integrin α8β1 is involved in diseases and tissue morphogenesis, but fail to disclose a functional inhibitor for integrin α8β1, a therapeutic agent, or a diagnostic agent so as to improve the above phenomena. In order to obtain the therapeutic or diagnostic agent which exerts a novel mechanism of action or an effect, it has been required to reveal a substance capable of inhibiting an integrin α8β1 function or a substance capable of being used for treatment or diagnosis by exerting an effect on integrin α8β1.

Non-Patent Document 3 describes that an antibody binding to an integrin and inhibiting its functions has exerted a therapeutic effect on a disease. This effect, however, is involved only with integrin α4β1, and there is no disclosure regarding integrin α8β1. It has been known that integrins have different functions depending on the types of α chain or β chain (Hynes R O., Cell, 2002, Sep. 20, 110(6), 673-87). In order to obtain a therapeutic or diagnostic agent which has a novel mechanism of action or an effect, it has been necessary to reveal an antibody binding to integrin α8β1 and inhibiting its function.

Embodiments of Patent Document 1 include integrin α8β1 as a candidate for an integrin binding to an Fc variant of an anti-integrin αVβ3 antibody. Patent Document 1, however, discloses nothing about experimental data to prove that. In addition, even if the content of Patent Document 1 is taken into consideration, it is difficult to produce the above Fc variant which binds to integrin α8β1.

The Claims of Patent Document 2 set forth integrin α8β1 as a candidate for an antigen against a recombinant human immunoglobulin having an antigen-binding region containing a specific amino acid sequence. Patent Document 2, however, discloses nothing about experimental data to prove that. In addition, even if the content of Patent Document 2 is taken into consideration, it is difficult to produce the above recombinant human immunoglobulin which binds to integrin α8β1.

Non-Patent Document 4 describes antibodies against integrin α8β1, but any of those antibodies has been produced as a mouse antibody. Accordingly, those antibodies are presumed not to react with mouse integrin α8β1. For development of a therapeutic or diagnostic agent, etc., it is common to examine their effects on organisms such as a human, a mouse, and a rat. Consequently, an antibody having cross-reactivity toward these organisms is needed. Among them, many mouse strains have a known genetic background, and also have a property of a short generation time. Further, a mouse is susceptible to diseases similar to those of a human, and is thus an important organism. In order to obtain a therapeutic or diagnostic agent which exerts a novel mechanism of action or an effect, it has been required to reveal an anti-integrin α8β1 antibody having cross-reactivity toward multiple species. In particular, it has been necessary to reveal an anti-integrin α8β1 antibody which cross-reacts with a mouse.

The present invention has been made in light of the above situation. It is an object of the present invention to provide an anti-integrin α8β1 antibody having an effect of inhibiting binding between integrin α8β1 and its ligand. In addition, it is another object of the present invention to provide an anti-integrin α8β1 antibody which binds to integrin α8β1 derived from mammals of different species. Furthermore, it is another object of the present invention to provide a process for producing an antibody having a novel property.

Means for Solving the Problems

An aspect of the present invention provides an anti-integrin α8β1 antibody which inhibits binding between integrin α8β1 and its ligand.

An Example as described below demonstrates that this anti-integrin α8β1 antibody exerts an effect of inhibiting the binding between integrin α8β1 and its ligand. Because of this, use of this anti-integrin α8β1 antibody enables the binding between integrin α8β1 and its ligand to be inhibited depending on various objects such as a therapeutic or diagnostic agent.

In addition, an aspect of the present invention provides an anti-integrin α8β1 antibody which binds to integrin α8β1 derived from mammals of different species.

An Example as described below demonstrates that this anti-integrin α8β1 antibody exerts an effect of binding to integrin α8β1 derived from mammals of different species. This results in production of an anti-integrin α8β1 antibody having cross-reactivity toward integrin α8β1 derived from mammals of different species.

In addition, an aspect of the present invention provides an anti-integrin α8β1 antibody comprising an antibody heavy chain variable region comprising heavy chain CDR1 having an amino acid sequence set forth in SEQ ID No: 1, heavy chain CDR2 having an amino acid sequence set forth in SEQ ID No: 2, and heavy chain CDR3 having an amino acid sequence set forth in SEQ ID No: 3. In addition, an aspect of the present invention provides an anti-integrin α8β1 antibody comprising an antibody heavy chain variable region comprising heavy chain CDR1 having an amino acid sequence set forth in SEQ ID No: 4, heavy chain CDR2 having an amino acid sequence set forth in SEQ ID No: 5, and heavy chain CDR3 having an amino acid sequence set forth in SEQ ID No: 6. In addition, an aspect of the present invention provides an anti-integrin α8β1 antibody comprising an antibody heavy chain variable region comprising heavy chain CDR1 having an amino acid sequence set forth in SEQ ID No: 7, heavy chain CDR2 having an amino acid sequence set forth in SEQ ID No: 8, and heavy chain CDR3 having an amino acid sequence set forth in SEQ ID No: 9.

An Example as described below demonstrates that these anti-integrin α8β1 antibodies exert an effect of inhibiting the binding between integrin α8β1 and its ligand. Because of this, use of these anti-integrin α8β1 antibodies enables the binding between integrin α8β1 and its ligand to be inhibited depending on various objects such as a therapeutic or diagnostic agent. In addition, these anti-integrin α8β1 antibodies have been demonstrated to exert an effect of binding to integrin α8β1 derived from mammals of different species. This results in production of an anti-integrin α8β1 antibody having cross-reactivity toward integrin α8β1 derived from mammals of different species.

Also, even if each of the above SEQ ID Nos: 1, 4, and 7 is subjected to one amino acid deletion, substitution, or addition, those skilled in the art can easily expect that a similar effect is reasonably achieved. Additionally, even if each of the above SEQ ID Nos: 2, 3, 5, 6, 8, and 9 is subjected to 1 to 3 amino acid deletions, substitutions, or additions, those skilled in the art can easily expect that a similar effect is reasonably achieved.

In addition, an aspect of the present invention provides a polynucleotide comprising a nucleotide sequence encoding an anti-integrin α8β1 antibody which inhibits binding between integrin α8β1 and its ligand.

This polynucleotide comprises a nucleotide sequence encoding an anti-integrin α8β1 antibody which has been demonstrated in an Example below to exert an effect of inhibiting the binding between integrin α8β1 and its ligand. This results in production of an anti-integrin α8β1 antibody from an antibody prepared based on this polynucleotide, the antibody inhibiting the binding between integrin α8β1 and its ligand.

In addition, an aspect of the present invention provides a polynucleotide comprising a nucleotide sequence encoding an anti-integrin α8β1 antibody which binds to integrin α8β1 derived from mammals of different species.

This polynucleotide comprises a nucleotide sequence encoding an anti-integrin α8β1 antibody which has been demonstrated in an Example below to bind to integrin α8β1 derived from mammals of different species. This results in production of an anti-integrin α8β1 antibody from an antibody prepared based on this polynucleotide, the antibody binding to integrin α8β1 derived from mammals of different species.

In addition, an aspect of the present invention provides an inhibitor of binding between integrin α8β1 and its ligand, the inhibitor comprising an anti-integrin α8β1 antibody which inhibits the binding between integrin α8β1 and its ligand or an anti-integrin α8β1 antibody which binds to integrin α8β1 derived from mammals of different species.

This inhibitor of binding between integrin α8β1 and its ligand contains an anti-integrin α8β1 antibody which has been demonstrated in an Example below to exert an effect of inhibiting the binding between integrin α8β1 and its ligand. Because of this, use of this inhibitor of binding between integrin α8β1 and its ligand enables the binding between integrin α8β1 and its ligand to be inhibited depending on various objects such as a therapeutic or diagnostic agent.

In addition, an aspect of the present invention provides a therapeutic agent comprising an anti-integrin α8β1 antibody which inhibits binding between integrin α8β1 and its ligand or an anti-integrin α8β1 antibody which binds to integrin α8β1 derived from mammals of different species, wherein the therapeutic agent is used for one or more diseases selected from the group consisting of cancer, arthritis, glaucoma, and neuropathic pain.

This therapeutic agent contains an anti-integrin α8β1 antibody which has been demonstrated in an Example below to exert an effect of inhibiting the binding between integrin α8β1 and its ligand. When functions of PI3K or FAK, which acts downstream of an integrin α8β1-mediated signal transduction mechanism, are inhibited by an antagonist (Yaguchi et al., J Natl Cancer Inst., 2006, Apr. 19, 98(8), 545-56), it is described that a therapeutic effect has been exerted in vivo on an animal model for cancer. Also, it is described that a therapeutic effect has been exerted in vivo on an animal model for non-small cell lung carcinoma (Boehle et al., Langenbecks Arch Surg., 2002, October, 387(5-6), 234-9 (Epub, Sep. 28, 2002)), arthritis (Tamura et al., Jpn J Clin Immunol., 2007, 30(5), 369-374), neuropathic pain (JP2007-63205A), or glaucoma (JP2003-104909A). Hence, this therapeutic agent can achieve a therapeutic effect on cancer, arthritis, glaucoma, or neuropathic pain by inhibiting signaling through integrin α8β1 to PI3K or FAK.

In addition, an aspect of the present invention provides a diagnostic agent comprising an anti-integrin α8β1 antibody which inhibits binding between integrin α8β1 and its ligand or an anti-integrin α8β1 antibody which binds to integrin α8β1 derived from mammals of different species, wherein the diagnostic agent is used for one or more diseases selected from the group consisting of pulmonary fibrosis, hepatic fibrosis, renal failure, and inner ear disease.

This diagnostic agent contains an anti-integrin α8β1 antibody which has been demonstrated in an Example below to exert an effect of inhibiting the binding between integrin α8β1 and its ligand or an anti-integrin α8β1 antibody which has been demonstrated in an Example below to bind to integrin α8β1 derived from mammals of different species. It is described that integrin α8β1 is highly expressed in pulmonary fibrosis or hepatic fibrosis (Levine et al., Am J Pathol., 2000, June, 156(6), 1927-35). Also, in an integrin α8 chain-knockout mouse, it has been described that kidney morphogenesis failure happens (Muller et al., Cell, 1997, Mar. 7, 88(5), 603-13), and inner hair cell deficiency occurs (Littlewood et al., Nat Genet., 2000 April, 24(4), 424-8). Accordingly, use of this diagnostic agent along with a diagnosis protocol known in the art allows for diagnosis of renal failure caused by kidney morphogenesis failure, inner ear disease occurring in inner hair cells, pulmonary fibrosis, or hepatic fibrosis.

In addition, an aspect of the present invention provides a diagnostic agent comprising an anti-integrin α8β1 antibody which inhibits binding between integrin α8β1 and its ligand or an anti-integrin α8β1 antibody which binds to integrin α8β1 derived from mammals of different species, wherein the diagnostic agent is used for one or more diseases selected from the group consisting of cancer, arthritis, glaucoma, and neuropathic pain.

This diagnostic agent contains an anti-integrin α8β1 antibody which has been demonstrated in an Example below to exert an effect of inhibiting the binding between integrin α8β1 and its ligand or an anti-integrin α8β1 antibody which has been demonstrated in an Example below to bind to integrin α8β1 derived from mammals of different species. As described herein above, when functions of PI3K or FAK, which acts downstream of an integrin α8β1-mediated signal transduction mechanism, are inhibited by an antagonist, it is described that a therapeutic effect has been exerted in vivo on an animal model for cancer, arthritis, glaucoma, or neuropathic pain. Accordingly, use of this diagnostic agent along with a diagnosis protocol known in the art allows for diagnosis of cancer, arthritis, glaucoma, or neuropathic pain.

In addition, an aspect of the present invention provides a process for producing an antibody, the process comprising the step of immunizing a chicken with an antigen containing antigenic protein-expressing cells or an antigen containing a cell membrane having an antigenic protein.

This production process has been proved in a below-described Example to be able to produce an antibody having properties different from those of antibodies as obtained using a conventional production process. Consequently, use of this production process can produce an antibody having properties different from those of antibodies as obtained using a conventional production process.

Effects of the Invention

Embodiments of the present invention provide anti-integrin α8β1 antibodies which inhibit binding between integrin α8β1 and its ligand, anti-integrin α8β1 antibodies which bind to integrin α8β1 derived from mammals of different species, or inhibitors of binding between integrin α8β1 and its ligand, the inhibitors containing an anti-integrin α8β1 antibody. In addition, embodiments of the present invention allow for a process for producing an antibody having a novel property.

MODES FOR CARRYING OUT THE INVENTION

<History of the Invention>

The present inventors have been conducting research which aims to functionally analyze integrin α8β1 and to improve performance of an anti-integrin α8β1 antibody so as to develop a therapeutic agent, a diagnostic agent, or a research reagent (material). A correlation with various diseases has been reported, including that integrin α8β1 is involved in kidney morphogenesis and is highly expressed in a mouse lung affected by pulmonary fibrosis. Unfortunately, details on physiological functions remain unresolved in many points.

In such a situation, the present inventors have sought for an anti-integrin α8β1 antibody. During production of the antibody, various points have been considered, including an immune animal, panning selection, and the like.

Then, when the resulting antibody has been examined regarding its cross-reactivity, the antibody, remarkably, binds to integrin α8β1 derived from both a human and a mouse. In addition, the antibody has an activity of inhibiting the binding between integrin α8β1 and its ligand. Accordingly, an antibody exerting an effect which cannot be previously predicted has been successfully obtained, and the present invention has been completed.

<Description of Terms>

The meanings of various terms as used herein will be described below.

(1) Integrin

Figure 1:
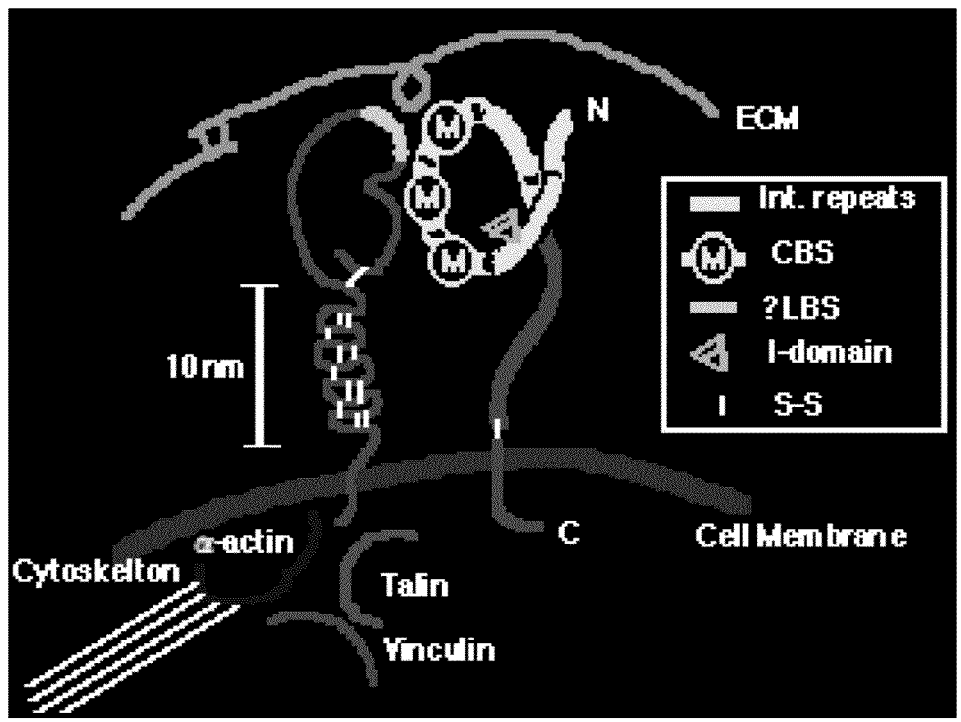
FIG. 1 is a typical conceptual diagram illustrating an integrin on a cell membrane.
Figure 2:
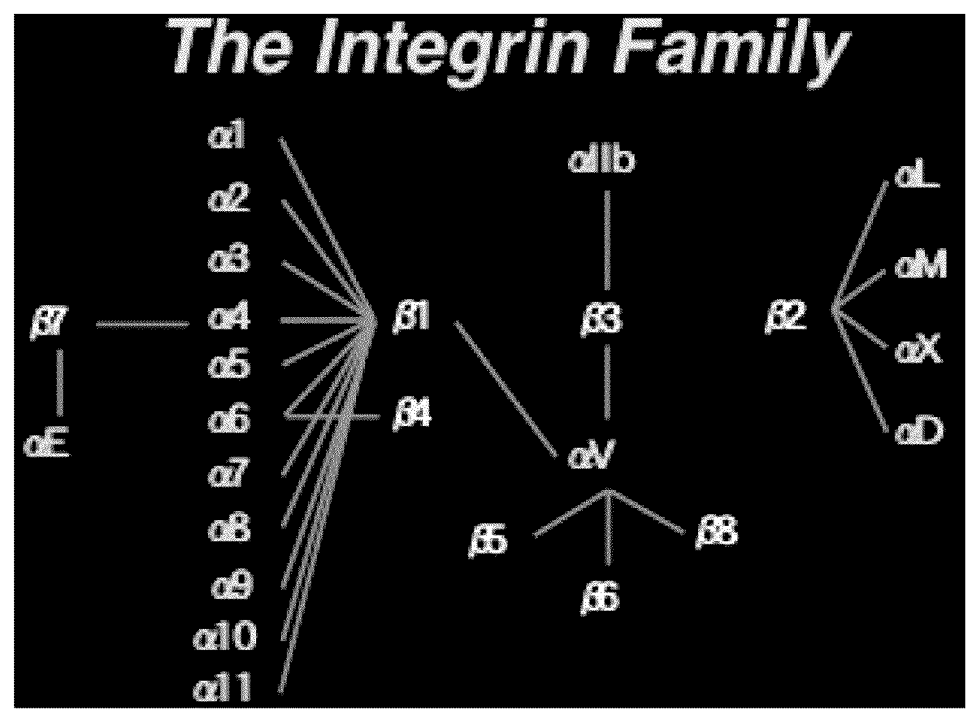
FIG. 2 is a diagram for matching integrin a chains with β chains.
Figure 3:
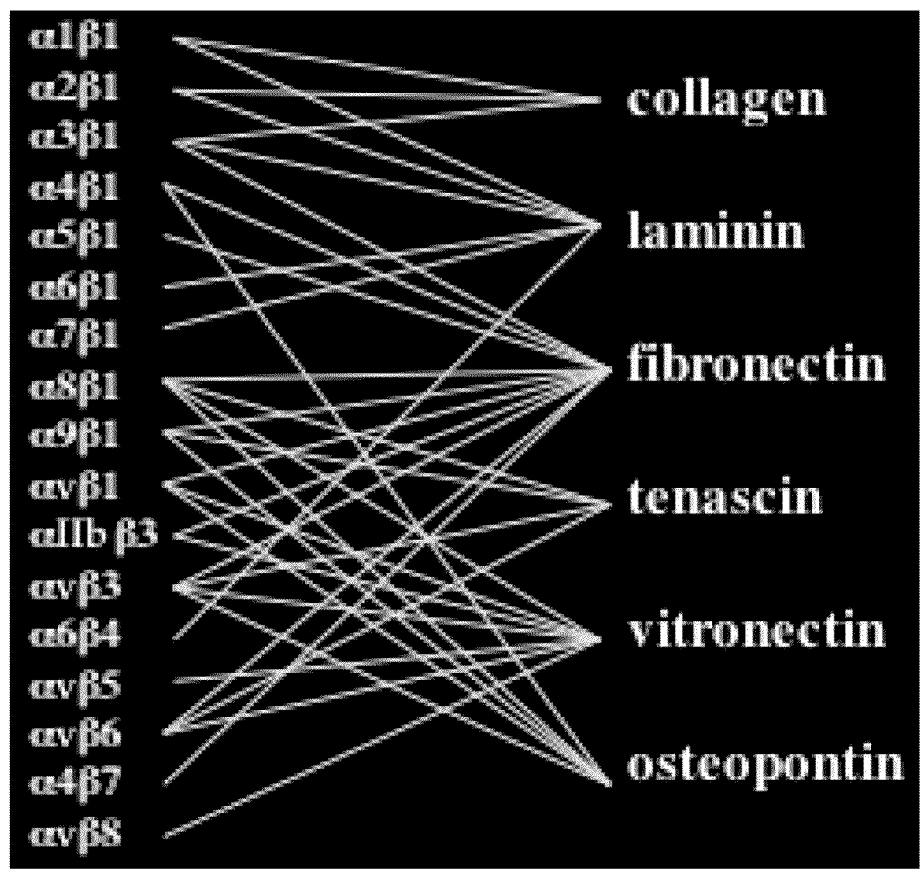
FIG. 3 is a diagram for matching integrins with their ligands.

An integrin is a receptor present on the surface of a plasma membrane as a heterodimer consisting of an α chain and a β chain. The integrin has been reported to function mainly as a receptor for an extracellular matrix. Its ligand binding triggers binding of its cytoplasmic domain to a molecule such as FAK or talin, and transmits a signal into a nucleus (FIG. 1). Its subunits include 18 α chains and 8 β chains. A total of 24 kinds of the integrin are known to exist (FIG. 2). Although each integrin has ligand selectivity, its ligand overlaps (FIG. 3). Deletion of any subunit causes either lethality or phenotypic changes. Accordingly, every subunit is said to be indispensable for survival or health maintenance. In addition, normal cells contact some extracellular matrix, and an integrin-mediated signal is said to be constitutively transduced. If the composition of the matrix surrounding a cell is changed, the cell recognizes such a change via integrins. Also, the integrins have a crosstalk with a growth factor signal, and are known to function cooperatively. There are many reports that the integrin signal plays a role in cell differentiation, cell proliferation, cell death, or the like.

(2) Integrin α8β1

Integrin α8 chain and β1 chain form a heterodimer. This integrin is known to have specificity for a ligand containing an RGD motif, the ligand including fibronectin, vitronectin, tenascin, osteopontin, or the like. The integrin α8 chain is expressed in kidney mesangial cells, vascular smooth muscle cells, fibroblasts, or the like. Experiments using its knockout mouse reportedly demonstrate that in particular, this integrin is critical in kidney morphogenesis (Muller et al., Cell, 1997, Mar. 7, 88(5), 603-13). There are several reports suggesting a correlation with a disease, the correlation including that the integrin α8 chain is highly expressed in a narrowed part of an artery in a rat after vascular disorder or in a lung of a mouse affected by pulmonary fibrosis (Levine et al., Am J Pathol., 2000, June, 156(6), 1927-35). Detailed physiological functions of this integrin remain unresolved in many points.

Hereinafter, embodiments of the present invention will be described in detail. Descriptions are not repeated so as to avoid redundancy.

(1) Anti-Integrin α8β1 Antibody

An embodiment of the present invention provides anti-integrin α8β1 antibodies. The above anti-integrin α8β1 antibodies include an anti-integrin α8β1 antibody that inhibits binding between integrin α8β1 and its ligand. Accordingly, use of the above anti-integrin α8β1 antibody seems to be able to inhibit various functions that are responsible for signal transduction involved with integrin α8β1, the functions including, for example, PI3K (phosphoinositide 3-kinase) activation (Hynes R O., Cell, 2002, Sep. 20, 110(6), 673-87; Farias et al., Biochem Biophys Res Commun., 2005, Apr. 1, 329(1), 305-11) and FAK (focal adhesion kinase) activation (Richard et al., Cell, Vol. 110, 673-687, Sep. 20, 2002; Shou-chun Liu, Journal of Cell Science, 113, 3563-3571 (2000); Littlewood et al, Nat Genet., 2000, April, 24(4), 424-8).

The above anti-integrin α8β1 antibodies may include an anti-integrin α8β1 antibody that binds to integrin α8β1 derived from mammals of different species. In this case, use of the above anti-integrin α8β1 antibody as a detection probe enables the localization of integrin α8β1 to be investigated in mammalian tissues and cells etc. In addition, the above anti-integrin α8β1 antibody can be suitably used as a component for an agent (e.g., a therapeutic agent) that is important to examine its effect on multiple organisms.

In addition, the integrin α8β1 binding to the above anti-integrin α8β1 antibody may be integrin α8β1 derived from a human and any of one or more organisms preferably selected from a mouse, a rat, a guinea pig, a rabbit, a pig, a sheep, cattle, a horse, a cat, a dog, a monkey, and a chimpanzee. This is because at the time of development of a therapeutic or diagnostic agent for a human disease, a mouse, a rat, a rabbit, a pig, a sheep, cattle, a horse, a cat, a dog, a monkey, or a chimpanzee may serve as a mammal which can be used as a typical disease model animal. In addition, the foregoing mammal may include a human and any of one or more organisms more preferably selected from a mouse, a rat, a guinea pig, a monkey, and a chimpanzee. This is because a mouse, a rat, a guinea pig, a monkey, and a chimpanzee are commonly used in the world as a research model animal and many of their properties have been revealed. Among them, many mouse strains have a known genetic background, also have a property of a short generation time, and further are susceptible to diseases similar to those of a human. Hence, a mouse is preferable.

As used herein, the term "binding" means a link between substances. The link may be either a covalent bond or a noncovalent bond, and includes, for example, an ionic bond, a hydrogen bond, a hydrophobic interaction, or a hydrophilic interaction.

In addition, the above anti-integrin α8β1 antibodies may include a recombinant protein produced from cells derived from a human or another mammal (e.g., a rat, a mouse, a rabbit, cattle, a monkey, a pig, a horse, a sheep, a goat, a dog, a cat, a guinea pig, a hamster) having any of a polynucleotide encoding the above anti-integrin α8β1 antibody, a vector containing a polynucleotide encoding the above anti-integrin α8β1 antibody, and a vector containing a portion of a polynucleotide encoding the above anti-integrin α8β1 antibody. Examples of mammalian cells can include monkey COS-7 cells, Vero cells, Chinese hamster CHO cells (CHO cells), dhfr-deficient Chinese hamster CHO cells (CHO (dhfr) cells), mouse L cells, mouse AtT-20 cells, mouse myeloma cells, rat GH3 cells, human FL cells, human HEK293 cells, and the like. Alternatively, the above anti-integrin α8β1 antibodies may include a recombinant protein produced from *Escherichia* bacteria, *Bacillus* bacteria, yeasts, or insect cells.

In addition, examples of the above vector which can be used include *Escherichia coli*-derived plasmids (e.g., pBR322, pBR325, pUC12, pUC13), *Bacillus subtilis*-derived plasmids (e.g., pUB110, pTP5, pC194), yeast-derived plasmids (e.g., pSH19, pSH15), bacteriophages (e.g., a λ phage), animal viruses (e.g., a retrovirus, a vaccinia virus, a baculovirus), pA1-11, pXT1, pRc/CMV, pRc/RSV, pcDNAI/Neo, and the like.

Also, the above polynucleotide or vector can be introduced into cells and the antibody can be produced in accordance with a method known in the art. Examples of a method which can be used for expressing an antibody in a cell include a calcium phosphate method, lipofection, electroporation, an adenovirus-mediated method, a retrovirus-mediated method, microinjection, and the like ("Genetic Engineering Handbook", 4th Edition, YODOSHA CO., LTD. (2003): 152-179). Methods (described in, for example, "Protein Experiment Handbook", YODOSHA CO., LTD., (2003), 128-142; or Shimamoto et al., Biologicals, 2005, September, 33(3), 169-174) can be used as a process for producing an antibody by using cells. In addition, the above anti-integrin α8β1 antibodies may be a protein which is chemically synthesized or synthesized using a cell-free translation system.

In addition, the above anti-integrin α8β1 antibodies can be purified from anti-integrin α8β1 antibody-producing cells by using a method known in the art. Examples of a method for purifying an antibody include ammonium sulfate precipitation or ethanol precipitation, Protein A, Protein G, or gel filtration chromatography, anion or cation-exchange chromatography, phosphocellulose chromatography, hydrophobic interaction chromatography; affinity chromatography, hydroxylapatite chromatography, lectin chromatography, and the like ("Protein Experiment Handbook", YODOSHA CO., LTD., 2003, 27-52).

In addition, the above anti-integrin α8β1 antibodies include an antibody which binds to wild type or mutant integrin α8β1. As used herein, the term "mutant" includes being responsible for a DNA sequence variation among individuals. Also, the above anti-integrin α8β1 antibodies are preferably a wild type. In the case of a mutant, the mutant has preferably 80% or more homology to the wild type, more preferably 90% or more homology, and still more preferably 95% or more homology. This is because if the mutant has an amino acid sequence having higher homology to the wild type, functions similar to those of an anti-integrin α8β1 antibody which has been verified to inhibit the binding between integrin α8β1 and its ligand are obtained.

As used herein, the term "homology" refers to a ratio of the number of identical amino acids between two or among a plurality of amino acid sequences to the total number of amino acids as calculated by using a process known in the art. Before the calculation of the ratio, amino acid sequences selected from the group of amino acid sequences compared are aligned. If the ratio of the identical amino acids is required to be optimized, gaps are inserted in some portions of the amino acid sequence. In addition, any conservative substitution is not considered to be identical. Also, the term means a ratio of the number of identical amino acids to the total number of amino acid residues including overlapping amino acids while keeping the optimal alignment. An alignment method, a ratio calculation process, and a related computer program are conventionally well known in the art. A common sequence analysis program (e.g., GENETYX, Gene Chip Sequence Analysis) can be used for measurements.

The above anti-integrin α8β1 antibodies may include an anti-integrin α8β1 antibody whose heavy chain variable region comprises heavy chain CDR1 having an amino acid sequence set forth in SEQ ID No: 1, heavy chain CDR2 having an amino acid sequence set forth in SEQ ID No: 2, and heavy chain CDR3 having an amino acid sequence set forth in SEQ ID No: 3. In this case, the antibody light chain variable region of the foregoing anti-integrin α8β1 antibody may comprise light chain CDR1 having an amino acid sequence set forth in SEQ ID No: 10, light chain CDR2 having an amino acid sequence set forth in SEQ ID No: 11, and light chain CDR3 having an amino acid sequence set forth in SEQ ID No: 12.

In addition, the above anti-integrin α8β1 antibodies may include an anti-integrin α8β1 antibody whose heavy chain variable region comprises heavy chain CDR1 having an amino acid sequence set forth in SEQ ID No: 4, heavy chain CDR2 having an amino acid sequence set forth in SEQ ID No: 5, and heavy chain CDR3 having an amino acid sequence set forth in SEQ ID No: 6. In this case, the antibody light chain variable region of the foregoing anti-integrin α8β1 antibody may comprise light chain CDR1 having an amino acid sequence set forth in SEQ ID No: 13, light chain CDR2 having an amino acid sequence set forth in SEQ ID No: 14, and light chain CDR3 having an amino acid sequence set forth in SEQ ID No: 15.

In addition, the above anti-integrin α8β1 antibodies may include an anti-integrin α8β1 antibody whose heavy chain variable region comprises heavy chain CDR1 having an amino acid sequence set forth in SEQ ID No: 7, heavy chain CDR2 having an amino acid sequence set forth in SEQ ID No: 8, and heavy chain CDR3 having an amino acid sequence set forth in SEQ ID No: 9. In this case, the antibody light chain variable region of the foregoing anti-integrin α8β1 antibody may comprise light chain CDR1 having an amino acid sequence set forth in SEQ ID No: 16, light chain CDR2 having an amino acid sequence set forth in SEQ ID No: 17, and light chain CDR3 having an amino acid sequence set forth in SEQ ID No: 18. The anti-integrin α8β1 antibodies containing the above specific CDRs are demonstrated in the below-described Examples to inhibit the binding between integrin α8β1 and its ligand or to bind to any of human- and mouse-derived integrin α8β1.

Here, the amino acid sequences set forth in the above SEQ ID Nos: 1, 4, 7, 11, 14, and 17 may have one amino acid deletion, substitution, or addition of the respective amino acid sequences. Even in the case of there being such a deletion, etc., of the amino acid sequences included in the above anti-integrin α8β1 antibodies, a similar effect seems to be exerted, compared to that of the case of there being no deletion etc. Also, the above term "addition" includes a concept of insertion.

In addition, the amino acid sequences set forth in the above SEQ ID Nos: 2, 3, 5, 6, 8, and 9 may have one to three amino acid deletions, substitutions, or additions of the respective amino acid sequences. Even in the case of there being such a deletion, etc., of the amino acid sequences included in the above anti-integrin α8β1 antibodies, a similar effect seems to be exerted, compared to that of the case of there being no deletion etc. As used herein, the above term "one to three" refers to preferably "one to two", and more preferably "one". This is because when the above "one to three" refers to a less number, it indicates that the antibody has properties more similar to those of the anti-integrin α8β1 antibody without deletion, etc., of its amino acid sequence.

In addition, the amino acid sequences set forth in the above SEQ ID Nos: 10, 12, 13, 15, 16, and 18 may have one to two amino acid deletions, substitutions, or additions of the respective amino acid sequences. Even in the case of there being such a deletion, etc., of the amino acid sequences included in the above anti-integrin α8β1 antibodies, a similar effect seems to be exerted, compared to that of the case of there being no deletion etc. As used herein, the above term "one to two" refers to preferably "one". This is because when the above "one to two" refers to a less number, it indicates that the antibody has properties more similar to those of the anti-integrin α8β1 antibody without deletion of its amino acid sequence. In addition, in the amino acid sequence set forth in SEQ ID No: 15, any amino acid can be used for amino acids denoted by Xaa.

When one-letter amino acid codes (capital letters) are used to represent identical amino acid sequences among CDR sequences of the anti-integrin α8β1 antibodies including antibody No. 3, No. 5, and No. 26 which have been actually obtained in the below-described Examples, the heavy chain CDR1 contains xxDMx (SEQ ID No: 19), the heavy chain CDR2 contains IxxxxSxxxYxxAVKG (SEQ ID No: 20), the heavy chain CDR3 contains xxxxYxxxGxxxxxxxID (SEQ ID No: 21), the light chain CDR1 contains SGxxxSxYG (SEQ ID No: 22), the light chain CDR2 contains xxxxRPS (SEQ ID No: 23), and the light chain CDR3 contains Gxxxxxxxxxxx (SEQ ID No: 24), The symbol "x" represents an amino acid which is different from or deleted from the standard amino acid sequence set forth in that of the antibody No. 3. When the above anti-integrin α8β1 antibodies according to embodiments of the present invention have a deletion, etc., the position of the deletion, etc., may correspond to a region represented by the above symbol "x".

In addition, the above anti-integrin α8β1 antibodies may be encoded by plasmids including Accession No: NITE BP-824, Accession No: NITE BP-825, Accession No: NITE BP-826, Accession No: NITE BP-827, Accession No: NITE BP-828, or Accession No: NITE BP-829. Also, the above anti-integrin α8β1 antibodies may comprise an amino acid sequence of or an amino acid sequence having 80% or more homology to a heavy chain $V_H$, heavy chain CDR 1 to 3, light chain $V_L$, or light chain CDR 1 to 3 of antibodies encoded by the above plasmids. Of note is that the above term "80% or more" refers to preferably having 85% or more, more preferably having "90% or more", and still more preferably having 95% or more. This is because the higher the homology is, the more their properties are similar to those of the antibodies encoded by the above plasmids.

By the way, the DNA sequence and the amino acid sequence of integrin α8β1 are publicly known. For example, GenBank, a database of National Center for Biotechnology Information (NCBI), etc., can be used for reference.

As used herein, the term "antibody" refers to a molecule which specifically binds to a specific epitope localized on an antigen, and the term includes a polyclonal antibody and a monoclonal antibody. In addition, the antibody can exist as various forms. Examples of the forms can include Fv, Fab, F(ab')2, Fab', a diabody, a single-chain antibody (e.g., scFv, dsFv), a CDR-containing peptide, a multivalent antibody (e.g., a divalent antibody), a mouse chimeric antibody, a chicken chimeric antibody, a humanized antibody, a human antibody, and the like. Also, the forms having a low-molecular-weight antibody or sugar-chain-modified antibody combined with a chemically synthesized existing pharmaceutical agent or pharmaceutical product may be allowed. In order to decrease immunogenicity when the antibody is used as a therapeutic agent, it is preferable for the antibody to have a high proportion of a human-derived amino acid sequence. Specifically, the antibody is preferably a chimeric antibody with human-derived regions, more preferably a humanized antibody, and most preferably a human antibody. In addition, in order to decrease immunogenicity or increase stability when the antibody is used as a therapeutic agent, it is preferable for the antibody to be a lower-molecular-weight molecule as long as the antibody possesses desired functions.

A polyclonal antibody described herein can be generated by administering an immunogen containing a target antigen to a mammal (e.g., a rat, a mouse, a rabbit, a chicken, cattle, a monkey, a pig, a horse, a sheep, a goat, a dog, a cat, a guinea pig, a hamster) or a bird (e.g., a chicken) so as to induce production of a serum containing an antigen-specific polyclonal antibody. Administration of the immunogen may require coinjection of one or more immunizing agents and an adjuvant as desired. The adjuvant may be used for enhancing an immune response. Examples of the adjuvant include (complete or incomplete) Freund adjuvant, a mineral gel (e.g., aluminum hydroxide), a surfactant (e.g., lysolecithin, pluronic polyol, a polyanion, a peptide, oil emulsion, keyhole limpet hemocyanin, dinitrophenol), and a potentially useful human adjuvant (e.g., Bacille Calmette-Guerin (BCG) or *Corynebacterium parvum*). In addition, the examples further include MPL-TDM adjuvant (monophosphoryl lipid A, synthetic trehalosedicorynomycolate) as well. An immunization protocol is publicly known in the art. Any method for inducing an immune response in a selected host animal may be carried out ("Protein Experiment Handbook", YODOSHA CO., LTD. (2003), 86-91).

As used herein, the term "monoclonal antibody" refers to an antibody collected from a substantially pure antibody population. That is, individual antibodies constituting a population include identical ones except the antibodies having mutations that can be present in a small number of cases and that can naturally occur. A monoclonal antibody is highly specific, and corresponds to one antigenic site. Further, the monoclonal antibody is distinct from a typical polyclonal antibody commonly containing different antibodies corresponding to different epitopes (antigen determinants). Each monoclonal antibody corresponds to a single epitope of an antigen. In addition to its specificity, the monoclonal antibody is useful in view of synthesizing the antibody by hybridoma culture without having contamination of other immunoglobulins. The modifier "monoclonal" indicates a feature of an antibody which has been obtained from a substantially pure antibody population, but does not mean that the antibody has to be produced by any particular method. For example, the monoclonal antibody described herein can be produced by a method similar to a hybridoma method disclosed in Kohler G and Milstein C., Nature, 1975, Aug. 7, 256 (5517), 495-497. Alternatively, the monoclonal antibody used in embodiments of the present invention can be produced by a method similar to the recombinant technology disclosed in U.S. Pat. No. 4,816,567. In addition, the monoclonal antibody used herein can be isolated from a phage antibody library by a method similar to the technology described in Clackson et al., Nature, 1991, Aug. 15, 352 (6336), 624-628 or Marks et al., J Mol Biol., 1991, Dec. 5, 222(3), 581-597. Furthermore, the antibody can be generated by a general production procedure disclosed in "Protein Experiment Handbook", YODOSHA CO., LTD., (2003), 92-96. Also, the monoclonal antibody used herein is preferably generated by a procedure described in Examples below.

Meanwhile, Fv is an antibody fragment containing a complete antigen-recognition and antigen-binding site. This Fv region consists of a dimer between variable domains of one heavy chain and one light chain which form tight non-covalent bonds. Using this arrangement, three CDRs of the respective variable domains interact with one another to form an antigen binding site on the surface of the $V_H$-$V_L$ dimer. Accordingly, these six CDRs give an antibody an antigen-binding specificity. Then, any known process can be employed as its production process. For example, the Fv can be produced by inserting a DNA encoding Fv of an anti-integrin α8β1 antibody described herein into a prokaryotic expression vector or a eukaryotic expression vector, and by introducing the vector into a prokaryote or a eukaryote to express the DNA.

In addition, Fab is an antibody fragment having an antigen-binding activity, the fragment being obtained by treating IgG with a protease, papain, and the fragment having the N-terminal half of the H chain and the entire L chain linked via a disulfide bond. Then, any known process can be employed as its production process. For example, the Fab can be produced by treating an anti-integrin α8β1 antibody with a protease, papain. Alternatively, the Fab can be produced by inserting a DNA encoding Fab of an anti-integrin α8β1 antibody into a prokaryotic expression vector or a eukaryotic expression vector, and by introducing the vector into a prokaryote or a eukaryote to express the DNA.

In addition, F(ab')2 is an antibody fragment having an antigen-binding activity, the fragment being obtained by treating IgG with a protease, pepsin, and the fragment having a little larger portion than Fabs whose hinge regions are linked via disulfide bonds. Then, any known process can be employed as its production process. For example, the F(ab')2 can be produced by treating an anti-integrin α8β1 antibody with a protease, pepsin. Also, the F(ab')2 can be produced by linking the following Fab's via a thioether bond or a disulfide bond.

In addition, Fab' is an antibody fragment having an antigen-binding activity, the fragment being produced by cleaving the disulfide bonds in the hinge regions of the F(ab')2. The Fab' can be produced by treating the F(ab')2 with a reducing agent, dithiothreitol. Then, any known process can be employed as its production process. For example, the Fab' can be produced by inserting a DNA encoding Fab' fragment of an anti-integrin α8β1 antibody described herein into a prokaryotic expression vector or a eukaryotic expression vector, and by introducing the vector into a prokaryote or a eukaryote to express the DNA.

In addition, scFv is an antibody fragment having an antigen-binding activity, the fragment being a polypeptide having one $V_H$ and one $V_L$ linked by a suitable peptide linker. Then, any known process can be employed as the production process. For example, the scFv can be produced by obtaining cDNAs encoding $V_H$ and $V_L$ of an anti-integrin α8β1 antibody described herein, by constructing a DNA encoding the scFv, by inserting the DNA into a prokaryotic expression vector or a eukaryotic expression vector, and by introducing the vector into a prokaryote or a eukaryote to express the DNA.

In addition, a diabody is an antibody fragment having divalent antigen-binding activities, the fragment having scFvs dimerized. Both of the divalent antigen-binding activities can be identical, or one of them can be a distinct antigen-binding activity. Then, any known process can be employed as its production process. For example, the diabody can be produced by obtaining cDNAs encoding $V_H$ and $V_L$ of an anti-integrin α8β1 antibody described herein, by constructing a DNA encoding scFv using a peptide linker whose length in its amino acid sequence is 8 residues or shorter, by inserting the DNA into a prokaryotic expression vector or a eukaryotic expression vector, and by introducing the vector into a prokaryote or a eukaryote to express the DNA.

In addition, dsFv is a general term referring to a polypeptide having one amino acid residue in the respective $V_H$ and the $V_L$ substituted by a cysteine residue, followed by linking the cysteine residues via a disulfide bond. The amino acid residue substituted by the cysteine residue can be selected based on an antibody conformation prediction in accordance with a procedure indicated by Reiter et al. (Reiter et al., Protein Eng., 1994, May, 7(5), 697-704). Then, any known process can be employed as its production-process. For example, the dsFv can be produced by obtaining cDNAs encoding $V_H$ and $V_L$ of an anti-integrin α8β1 antibody described herein, by constructing a DNA encoding the dsFv, by inserting the DNA into a prokaryotic expression vector or a eukaryotic expression vector, and by introducing the vector into a prokaryote or a eukaryote to express the DNA.

In addition, a peptide containing a CDR includes at least one CDR of either $V_H$ or $V_L$. A plurality of peptides containing a CDR can be linked directly or indirectly via a suitable peptide linker. Then, any known process can be employed as its production process. For example, the peptide containing a CDR can be produced by constructing a DNA encoding a CDR of $V_H$ or $V_L$ of an anti-integrin α8β1 antibody described herein, by inserting the DNA into a prokaryotic expression vector or a eukaryotic expression vector, and by introducing the vector into a prokaryote or a eukaryote to express the DNA. In addition, the peptide containing a CDR can also be produced by a chemical synthesis process such as an Fmoc (fluorenylmethyloxycarbonyl) process and a tBOC (t-butyloxycarbonyl) process.

In addition, a chimeric antibody can be produced by linking variable regions of an antibody derived from a non-human species to a constant region of a human antibody, and can be easily constructed using gene recombinant technology. A process for producing a chimeric antibody is known in the art. For example, a mouse-human chimeric antibody can be produced by a process disclosed in Roguska et al., Proc Natl Acad Sci USA., 1994, Feb. 1, 91(3), 969-973. The mouse-human chimeric antibody can be obtained by cloning DNA fragments encoding V regions of mouse light and heavy chains of a murine monoclonal antibody against a target antigen, by linking DNAs encoding these murine V regions to DNAs encoding constant regions of a human antibody, and by expressing the DNAs. A basic procedure for producing a mouse-human chimeric antibody includes: isolating a mouse leader sequence and a V region sequence present in a cloned cDNA; and linking these sequences to a sequence encoding a C region of a human antibody, the sequence being present in a mammalian expression vector. Alternatively, a murine leader sequence and a V region sequence present in a cloned cDNA are first linked to a sequence encoding a C region of a human antibody and the resulting sequence is then ligated into a mammalian expression vector. A fragment of the C region of the human antibody can be a C region of an H chain or a C region of an L chain of any human antibody. Examples of the C region of the human H chain can include Cγ1, Cγ2, Cγ3 and Cγ4. Examples of the C region of the L chain can include Cλ and Cκ.

In addition, a humanized antibody has one or more complementarity determining regions (CDRs) derived from a non-human species, human-immunoglobulin-derived framework regions (FRs), and human-immunoglobulin-derived constant regions. The humanized antibody binds to a desired antigen. In order to modify or, preferably, improve the antigen binding, amino acid residues in the human framework regions are frequently substituted by residues corresponding to those of the CDR-donor antibody. These framework substitutions are carried out using a procedure well-known in the art (e.g., by modeling of an interaction between CDR and framework residues so as to identify a critical framework residue for the antigen binding, and by sequence comparison so as to identify an abnormal framework residue in a particular position) (Riechmann et al., Nature, 1988, Mar. 24, 332(6162), 323-327). An antibody can be humanized by using various techniques known in the art (Almagro et al., Front Biosci., 2008, Jan. 1, 13, 1619-1633). Examples of the techniques can include CDR grafting (Ozaki et al., Blood, 1999, Jun. 1, 93(11), 3922-3930), re-surfacing (Roguska et al., Proc Natl Acad Sci USA., 1994, Feb. 1, 91(3), 969-973), and FR shuffling (Damschroder et al., Mol Immunol., 2007, April, 44(11), 3049-3060, Epub 2007, Jan. 22).

In addition, a human antibody has a heavy chain variable region, a heavy chain constant region, a light chain variable region, and a light chain constant region, all of which are derived from genes encoding a human immunoglobulin. The human antibody has less immunogenicity at the time of administration to a human, and can thus preferably be used for treatment of human diseases. Examples of a basic method for generating a human antibody include a method using a human-antibody-producing transgenic mouse, phage display, and the like. The method using a human-antibody-producing transgenic mouse includes: introducing a functional human Ig gene into an endogenous-Ig-knockout mouse; and producing, instead of a mouse antibody, a human antibody having versatile antigen-binding abilities. Further, if this mouse is immunized, a human monoclonal antibody can be obtained using a conventional hybridoma procedure. For example, the human antibody can be prepared using a method disclosed in Lonberg et al., Int Rev Immunol., 1995, 13(1), 65-93. The phage display is a system in which an exogenous gene is made to be expressed as a fusion protein at an N-terminal portion of a coat protein (e.g., g3p, g10p) of a filamentous phage such as M13 and T7, an *E. coli* virus, without losing infectivity of the phage. For example, the human antibody can be prepared using a method disclosed in Vaughan et al., Nat Biotechnol., 1996, March, 14(3), 309-314.

When one or several amino acids of the above anti-integrin α8β1 antibodies are substituted by other amino acids, the amino acids are preferably substituted by other amino acids which are conserved in their side chain characteristics. Examples of the characteristics of the amino acid side chain can include hydrophobic amino acids (e.g., A, I, L, M, F, P, W, Y, V), hydrophilic amino acids (e.g., R, D, N, C, E, Q, G, H, K, S, T), amino acids having an aliphatic side chain (e.g., G, A, V, L, I, P), amino acids having a hydroxy-containing side chain (e.g., S, T, Y), amino acids having a sulfur-containing side chain (e.g., C, M), amino acids having a carboxylic-acid-containing or amido-containing side chain (e.g., D, N, E, Q), amino acids having a base-containing side chain (e.g., R, K, H), and amino acids having an aromatic side chain (e.g., H, F, Y, W)(the respective letters between parentheses denote one-letter abbreviations of amino acids). A substitution of an amino acid by an amino acid within each group is generally referred to as a conservative substitution. It has been already known that a polypeptide having its amino acid sequence modified by one or several amino acid residue deletions, additions, or substitutions can maintain its biological activity (Mark et al., Proc Natl Acad Sci USA., 1984, September, 81(18), 5662-5666; Zoller et al., Nucleic Acids Res., 1982, Oct. 25, 10(20), 6487-6500; and Wang et al., Science, 1984, Jun. 29, 224(4656), 1431-1433).

In addition, the above anti-integrin α8β1 antibodies may be affinity-matured by using an existing selection or mutagenesis. An affinity-matured antibody has preferably 5 times higher affinity than a starting antibody, more preferably 10 times higher affinity, and still more preferably 20 or 30 times higher affinity. For example, biopanning utilizing an antibody phage library can be used. A typical manipulation of this method includes steps of: reacting an immobilized target protein with an antibody phage library; removing an unbound phage antibody by washing; eluting a bound phage antibody; and infecting *Escherichia coli* with the bound phage antibody. Repeating the above steps several times can produce a phage antibody specific to the target protein ("Antibody Experiment Manual", Revised Version, YODOSHA CO., LTD. (2008), 211-221).

Examples of a class of the above anti-integrin α8β1 antibodies include IgM, IgD, IgG, IgA, IgE, IgX, IgY, IgW, and IgNAR. Preferably, the class is IgM, IgD, IgG, IgA, or IgE. This is because IgM, IgD, IgG, IgA, and IgE are classes of a human-derived antibody. Thus, when the antibody is used as a therapeutic agent, its immunogenicity is highly likely to decrease.

In addition, the heavy chain CDR1, heavy chain CDR2, or heavy chain CDR3 of the above anti-integrin α8β1 antibodies may be derived from, for example, a human, another mammal (e.g., a rat, a mouse, a rabbit, cattle, a monkey, a pig, a horse, a sheep, a goat, a dog, a cat, a guinea pig, a hamster), or a bird (e.g., a chicken). In particular, those derived from a human or mouse are preferable. This is because those derived from a human can decrease immunogenicity at the time of administration to a human. A mouse is most frequently used for antibody production, so that information has been already accumulated. Besides, how to use the antibody is easier.

In addition, the above anti-integrin α8β1 antibodies can be obtained by isolating a DNA encoding CDRs of the heavy chain of the above anti-integrin α8β1 antibodies and a DNA encoding regions, other than the CDRs of the heavy chain, of a known antibody derived from a human or non-human organism, by ligating these DNAs into a vector in accordance with a procedure known in the art, and then by expressing these DNAs. At this time, in order to be able to increase efficiency of binding of an antibody to a target antigen, it is preferable to optimize regions except CDRs of the heavy chain of the antibody by using a process known in the art (e.g., a phage display or a process for screening an antibody having high reactivity by mutating, at random, amino acid residues of the antibody). In particular, because efficiency of binding of the antibody to a target antigen can be increased, FR regions are preferably optimized by using FR shuffling (Damschroder et al., Mol Immunol., 2007, April, 44(11), 3049-3060, Epub 2007 Jan. 22) or a process for substituting amino acid residues within a vernier zone and/or packaging residues (JP2006-241026A or Foote et al., J Mol Biol., 1992, Mar. 20, 224(2), 487-499).

Another embodiment of the present invention provides a process for producing an antibody. The above process for producing an antibody includes the step of immunizing a chicken with an antigen containing cells expressing an antigenic protein or an antigen containing a cell membrane having the antigenic protein. According to this production process, it is possible to produce an antibody recognizing an antigenic site different from a site in the case of using an antigen such as a short peptide fragment of the antigenic protein. In addition, the produced antibody that binds to the antigenic protein can be used as a therapeutic or diagnostic agent, etc., for various diseases involving the antigenic protein.

The above production process may further include the steps of: reacting a chicken-derived antibody library with the cells expressing the antigenic protein or the cell membrane having the antigenic protein; and selecting a bound antibody. In this case, an antibody having higher reaction specificity can be produced.

In the above production process, the above antigenic protein may be a membrane protein. In this case, an anti-membrane protein antibody can be produced. In addition, in the above production process, the above antigenic protein may be a membrane protein which forms a dimer. In this case, an antibody binding to a membrane protein which forms a dimer can be produced. Here, the dimer includes a heterodimer or a homodimer.

In addition, as to the above production process, the above antigenic protein may be an integrin α8 chain or integrin α8β1. The above antibody may be an anti-integrin α8β1 antibody. In this case, as demonstrated in the below-described Examples, an anti-integrin α8β1 antibody that inhibits the binding between integrin α8β1 and its ligand can be produced. In addition, an anti-integrin α8β1 antibody that binds to integrin α8β1 derived from any of a human and a mouse can be produced. In this case, as demonstrated in the below-described Examples, an anti-integrin α8β1 antibody that recognizes a site different from a site in the case of using a recombinant soluble integrin α8β1 as an antigen can be produced. Examples of the recombinant soluble integrin include a recombinant fusion protein between an integrin α8 chain and/or integrin β1 chain and an Fc region of an antibody.

In one hand, as to a process for producing an antibody conventionally used for a therapeutic agent, etc., the production process including the step of immunizing a mouse, etc., a species taxonomically related to a human, has become mainstream. On the other hand, the above production process includes the step of immunizing a chicken, a species taxonomically far from a human. Thus, the above production process has a feature distinct from that of the production process which has previously become main stream. Accordingly, in the case of using the above production process, an antibody having a structure different from that of an antibody generated from a mammal such as a mouse can be produced.

(2) Effects of Anti-Integrin α8β1 Antibody

Another embodiment of the present invention provides an inhibitor of binding between integrin α8β1 and its ligand, the inhibitor comprising the above anti-integrin α8β1 antibody. Inhibition of the binding between integrin α8β1 and its ligand seems to inhibit various functions induced by integrin α8β1-mediated signal transduction, the functions including, for example, PI3K activation (Hynes R O., Cell, 2002, Sep. 20, 110(6), 673-87; Farias et al., Biochem Biophys Res Commun., 2005, Apr. 1, 329(1), 305-11) and FAK activation (Richard et al., Cell, Vol. 110, 673-687, Sep. 20, 2002; Shouchun Liu., Journal of Cell Science, 113, 3563-3571, (2000); Littlewood et al., Nat Genet., 2000, April, 24 (4), 424-8).

It has been described that inhibition of PI3K functions has exerted an in vivo therapeutic effect on an animal model for cancer (Yaguchi et al., J Natl Cancer Inst., 2006, Apr. 19, 98(8), 545-56). Also, it is described that a therapeutic effect has been exerted in vivo on an animal model for non-small cell lung carcinoma (Boehle et al., Langenbecks Arch Surg., 2002, October, 387(5-6), 234-9 (Epub, Sep. 28, 2002)), arthritis (Tamura et al., Jpn J Clin Immunol., 2007, 30(5), 369-374), neuropathic pain (JP2007-63205A), or glaucoma (JP2003-104909A). Furthermore, it has been described that inhibition of FAK functions has an in vivo therapeutic effect on an animal model for pancreatic cancer (Hatakeyama et al., Journal of Clinical Oncology, Vol 24, No 18S (June 20, Supplement), 2006, 13162) or glioma (Liu et al., Mol Cancer Ther., 2007, April, 6(4), 1357-67).

That is, the above anti-integrin α8β1 antibody or the above inhibitor of binding between integrin α8β1 and its ligand, which inhibitor contains the above anti-integrin α8β1 antibody, inhibits functions of signaling molecules, such as PI3K or FAK, involving integrin α8β1. Through this inhibition, the above antibody or inhibitor can be suitably used as a therapeutic or diagnostic agent for the above diseases (e.g., cancer, arthritis, glaucoma, or neuropathic pain).

In addition, as used herein, the ligand for integrin α8β1 is not limited as long as the ligand is a substance interacting with integrin α8β1. The ligand, however, is preferably fibronectin, vitronectin, tenascin, or osteopontin. It is well known that they interact with integrin α8β1. Also, the subsequent integrin α8β1-mediated intracellular signal transduction mechanism is relatively better elucidated. Among the ligands, osteopontin is preferable. This is because osteopontin plays a critical role in diverse physiological effects so that it is an important molecule for development of a therapeutic agent etc. For example, osteopontin is involved in functions such as cell adhesion, cell migration, tumorigenesis, and immune responses. It is reported that its inhibition in vivo results in a therapeutic effect on arthritis (JP4064441B).

In addition, binding inhibition effects can be measured by any method known in the art, such as an ELISA, FACS analysis, and a BIACORE method. The results may be measured that the above anti-integrin α8β1 antibody competitively inhibits the binding in the presence of both integrin α8β1 and its ligand. Alternatively, the modes of the binding of the above anti-integrin α8β1 antibody to integrin α8β1 may be determined as an index for inhibition of binding between integrin α8β1 and its ligand. The measurements of the binding inhibition effects are preferably determined by a method described in the Examples below.

Here, the FACS analysis typically includes the steps of: irradiating a cell flowing inside a flow cell with a laser beam; measuring parameters as obtained from forward-scattered light and side-scattered light; and determining cellular properties. An amount of a fluorescence-labeled antibody binding to one cell is proportional to an amount of a surface antigen on the cell. Thus, the fluorescence intensity is proportional to the amount of the surface antigen.

Here, modes of binding of the above anti-integrin α8β1 antibody to integrin α8β1 can be represented by a dissociation constant (KD), an association constant (Ka), an association rate constant (ka), and a dissociation rate constant (kd). Of note is that the dissociation constant (KD) and the association constant (Ka) are static parameters at which a reaction is presumed to reach equilibrium. In practice, a reaction time is limited, so that almost no reaction reaches equilibrium. Accordingly, an antigen-antibody reaction at work is preferably evaluated by dynamic parameters such as an association rate constant (ka) or a dissociation rate constant (kd). An ELISA (Enzyme Linked Immuno-Sorbent Assay) or a BIACORE system can be used for the measurement. The ELISA can be implemented with a relatively low cost, and is the most common technique. The ELISA is an assay for determining a specific interaction, including: immobilizing, on a microplate, a predetermined amount of an antigen or antibody specifically reacting with a substance of measurement subject; adding the substance of measurement subject and an enzymatically labeled antigen together to react them; and measuring an enzymatic activity of the enzymatically labeled antigen bound to the microplate by using a colorimetric method or a fluorescence method. The assay utilizes a high binding capability and molecule-recognition capability of an antibody, so that detection can be achieved with very high sensitivity, compared with HPLC etc.

The BIACORE system is an excellent measurement method which can determine a dynamic parameter. The method includes: immobilizing a biomolecule on a sensor surface; applying an interaction partner molecule; and carrying out a real-time measurement of a specific interaction on the sensor surface. Without the need for labeling molecules, the BIACORE system can measure in real-time a specific interaction from an association reaction to an equilibrium state and a dissociation reaction. Measurement manipulations include: immobilizing a ligand on a sensor surface; applying a sample solution containing a reaction substance into a microchannel system; and measuring a specific interaction occurring on the sensor surface as a small mass change. The measurement principle employs an optical phenomenon, what is called surface plasmon resonance (SPR), so that a reliable measurement can be carried out. An association rate constant (ka) and a dissociation rate constant (kd) can be calculated based on reaction rates directly obtained, which allows for detailed analysis (Jonsson et al., Biotechniques, 1991, November, 11(5), 620-7; Fivash et Curr Opin Biotechnol., 1998, February, 9(1), 97-101; "Experiment Handbook of Instrumental Analysis for Life Science", YODOSHA CO., LTD., 2007, 243-248).

Meanwhile, strength of inhibition of binding between integrin α8β1 and its ligand by an anti-integrin α8β1 antibody can be evaluated by, for example, the following procedure. First, an anti-integrin α8β1 antibody is reacted with integrin α8β1-expressing cells. Next, the integrin α8β1-expressing cells after the reaction are made to react with osteopontin. Finally, the number of the integrin α8β1-expressing cells bound to osteopontin is determined by absorbance at 570 nm, and this procedure can thus evaluate the strength. At that time, absorbance as obtained in a negative control experiment (e.g., in the case without antibody treatment) can be set to a reference value which is designated as 0% of the binding inhibition strength. In addition, absorbance at the time of using cells which do not express integrin α8β1, instead of using the integrin α8β1-expressing cells, can be set to a reference value which is designated as 100% of the binding inhibition strength.

At this time, the binding inhibition strength of the above anti-integrin α8β1 antibody is, but not particularly limited to, for example, 5, 25, 50, 75, 95, or 100%. This binding inhibition strength may be any one of the above values or higher, or may be between any two of the above values.

The above activity of binding of an anti-integrin α8β1 antibody to integrin α8β1 can be estimated by FACS analysis and by calculating, as a positive rate, a ratio of the number of cells reacted with the test antibody to the total number of cells. This positive rate is, but not particularly limited to, for example, 5, 25, 50, 75, 95, or 100%. This positive rate may be any one of the above values or higher, or may be between any two of the above values.

As used herein, the term "treatment" refers to exerting a prophylactic effect or a symptom-improving effect on a disease of a subject individual or on one or more symptoms involving the disease.

Fibrosis refers to a symptom in which a tissue is damaged by some reason and becomes fibrous. Examples of the fibrosis include pulmonary fibrosis, hepatic fibrosis, myelofibrosis, cystic fibrosis, mammary gland fibrosis, and the like. In addition, the examples further include diseases that are classified into fibrosis-related diseases reported (in ICD10 international classification of disease, the 10th edition) by World Health Organization (WHO).

Renal failure refers to a symptom in which kidney functions decrease and the kidney no longer functions normally. In general, the renal failure is largely classified into acute renal failure and chronic renal failure. The chronic renal failure is a disease in which renal function damage chronically progresses. Examples of the chronic renal failure include those responsible for progression of chronic glomerulonephritis, diabetes mellitus, glomerulosclerosis, or interstitial fibrosis. Examples of the acute renal failure include prerenal acute renal failure, renal acute renal failure, postrenal acute renal failure, and the like. In addition, the examples further include those caused by allergy, toxicity, glomerular dysfunction, or tubulointerstitial disorder.

Inner ear disease includes a diseases resulting from disorders in organs, tissues, or nerves constituting an inner ear. Examples of the inner ear disease include labyrinthitis, Meniere's disease, diseases caused by a drug such as aspirin, hearing loss, streptomycin deafness, and the like. In addition, the examples further include diseases that are classified into inner ear-related diseases (in ICD10 international classification of disease, the 10th edition).

Arthritis refers to a joint inflammation-mediated disease having various symptoms such as pain, swelling, and heat. Examples of the arthritis include gouty arthritis, rheumatoid arthritis, psoriatic arthritis, osteochondritis dissecans, a knee disease, idiopathic osteonecrosis, deformans arthritis, septic arthritis, tuberculosis arthritis, hydrarthrosis, and the like. In addition, the examples further include diseases that are classified into arthritis-related diseases (in ICD10 international classification of disease, the 10th edition).

Cancer refers to a disease in which a normal cell is mutated and continues proliferation. A malignant cancer cell is generated from any organ or tissue in the body. Once the cancer cell proliferates, a solid consisting of the cancer tissue infiltrates into and destroys a surrounding normal tissue. Examples of the cancer include breast cancer, colorectal cancer, lung cancer, prostate cancer, hepatocarcinoma, gastric cancer, pancreatic cancer, cervical cancer, ovarian cancer, liver cancer, bladder cancer, ureteric cancer, thyroid cancer, kidney cancer, carcinoma, melanoma, brain tumor, and the like.

Glaucoma refers to an eye disease in which an increase in an intraocular pressure causes deficiency of a visual field. Examples of the glaucoma include primary glaucoma, congenital glaucoma, secondary glaucoma, and the like. In addition, the examples further include diseases that are classified into glaucoma-related diseases (in ICD10 international classification of disease, the 10th edition).

Neuropathic pain refers to pain resulting from primary damage or dysfunction of a nervous system or pain caused thereby. Examples of the neuropathic pain include postherpetic neuralgia, pain after cerebral infarction, low back pain, postoperative chronic pain, and the like. In addition, the examples further include those based on a neuropathic pain mechanism or a noxious pain mechanism.

In addition, the above anti-integrin α8β1 antibody or the inhibitor, which contains the above anti-integrin α8β1 antibody, of binding between integrin α8β1 and its ligand can be used as a therapeutic or prophylactic agent. In that case, sole administration may be allowed. However, one or more pharmaceutically acceptable carriers are usually mixed together. Then, it is preferable to provide a pharmaceutical preparation that is produced by any of the methods well known in the art of pharmaceutics. Alternatively, without directly using the above anti-integrin α8β1 antibody, a polynucleotide encoding the above anti-integrin α8β1 antibody or a vector thereof can be administered.

In addition, in terms of an administration route at the time of in vivo administration of the above anti-integrin α8β1 antibody, the most effective one for treatment is preferably used. Examples of the administration route include oral administration and parenteral administration such as intraoral, tracheobronchial, endorectal, subcutaneous, intramuscular, intraocular, and intravenous administration. Also, systemic or topical administration may be allowed. The administration route may be preferably intravenous administration. When the above anti-integrin α8β1 antibody exerts a desired function at affected tissues after oral administration, the oral administration is preferred.

Examples of an additional dosage form can include sprays, capsules, tablets, granules, syrups, emulsions, suppositories, injections, ointments, tapes, and the like. Examples of the formulation suitable for oral administration can include emulsions, syrups, capsules, tablets, powder medicines, granules, and the like. Liquid preparations such as emulsions and syrups can be prepared using additives including water, sugars (e.g., sucrose, sorbitol, fructose), glycols (e.g., polyethylene glycol, propylene glycol), oils (e.g., a sesame oil, an olive oil, a soy oil), preservatives (e.g., p-hydroxy benzoate esters), flavors (e.g., strawberry flavor, peppermint), and/or the like. Further, the capsules, tablets, powder medicines, or granules can be prepared using additives including excipients (e.g., lactose, glucose, sucrose, mannitol), disintegrants (e.g., starch, sodium alginate), lubricants (e.g., magnesium stearate, talc), binders (e.g., polyvinyl alcohol, hydroxypropylcellulose, gelatin), surfactants (e.g., fatty acid ester), plasticizers (e.g., glycerol), and/or the like.

Examples of the formulation suitable for parenteral administration can include injections, suppositories, sprays, and the like. Examples of an aqueous solution used for injections can include a saline and an isotonic solution containing glucose or another adjuvant such as D-sorbitol, D-mannose, D-mannitol, and sodium chloride. The adjuvant can be combined with a solubilization aid (e.g., alcohol (e.g., ethanol)), polyalcohol (e.g., propylene glycol, polyethylene glycol), and/or a nonionic surfactant (e.g., polysorbate 80™, HCO-50). The suppositories may be prepared using a carrier such as cacao butter, hydrogenated fat, or carboxylic acid. In addition, the sprays may be prepared using the inhibitor of binding between integrin α8β1 and its ligand and using a carrier, etc., which does not stimulate an oral cavity and respiratory tract mucosa of recipients and which makes the inhibitor of binding between integrin α8β1 and its ligand disperse as fine particles, so that the inhibitor is absorbed easily. Specific examples of this carrier include lactose, glycerol, and the like. Formulations such as aerosol and dry powder are allowed depending on characteristics of the carrier used and the inhibitor of binding between integrin α8β1 and its ligand. In addition, the components exemplified as additives for oral agents can be added to even these parenteral agents.

Also, the above prophylactic or therapeutic agent may be formulated with buffers (e.g., a phosphate buffer, a sodium acetate buffer), soothing agents (e.g., benzalkonium chloride, procaine hydrochloride), stabilizers (e.g., human serum albumin, polyethylene glycol), preservatives (e.g., benzyl alcohol, phenol), antioxidants, and/or the like. Prepared injections are usually filled in suitable ampules. Formulations as obtained in such a manner are safe and less toxic. Accordingly, the formulations can be administered to a human or mammals (e.g., a rat, a mouse, a rabbit, a sheep, a pig, cattle, a cat, a dog, a monkey).

In addition, an administration procedure can be appropriately selected depending on an age, a symptom, an affected organ, etc., of a patient. The dose of a pharmaceutical composition containing the above anti-integrin α8β1 antibody or a polynucleotide encoding the above anti-integrin α8β1 antibody can be selected from, for example, a range between 0.0001 mg and 1000 mg per kg body weight. Alternatively, the dose can be selected from, but is not necessarily limited to, a range between 0.001 and 100000 mg per patient body. The dose per kg body weight is, for example, 0.0001, 0.01, 1, 50, 100, 250, 500, or 1000 mg. This dose may be within a range between any two values indicated herein. The dose is different depending on an intended therapeutic effect, an administration procedure, a treatment period, an age, a body weight, or the like. The dose and administration procedure vary depending on a body weight, an age, and a symptom, etc. of a patient. However, those skilled in the art can appropriately select them. In addition, the administration may be combined with a suitable chemotherapeutic agent.

In addition, when a therapeutic objective resides in the brain and a therapeutic agent is required to pass through the blood-brain barrier (BBB), it is preferable to employ a drug design, an administration route, or an administration method which allows for passage through the BBB. Alternatively, the above anti-integrin α8β1 antibody may be modified into a form which allows for passage through the BBB. As for these methods, a method known in the art can be used. Examples of the method can include a method for extending gaps in the BBB, a method for using a membrane protein expressed in the BBB, a CED (convection-enhanced delivery) method, and the like (see a review by Bidros et al., Neurotherapeutics, 2009, July, 6(3), 539-46).

Another embodiment of the present invention provides a diagnostic agent for various diseases involving integrin α8β1 or a diagnostic agent comprising the above anti-integrin α8β1 antibody or the inhibitor of binding between integrin α8β1 and its ligand, the inhibitor containing the above anti-integrin α8β1 antibody, wherein the diagnostic agent is used for one or more diseases selected from the group consisting of cancer, arthritis, glaucoma, and neuropathic pain. This diagnostic agent contains the above anti-integrin α8β1 antibody, so that the diagnostic agent can be suitably used for diagnosis of various diseases involving integrin α8β1.

As used herein, usage of the diagnostic agent is not particularly limited. However, the diagnosis of the above diseases seems to be executed by examining and comparing the modes of binding of the antibody to integrin α8β1 between standard cells, etc., and materials such as cells, blood, serum, body fluid, or pathologic sections of any of the above diseases. For example, when high expression of integrin α8β1 is responsible for the diseases, the binding level of the antibody increases. When high expression of its ligand is responsible, it seems that competition with the ligand causes the binding level of the antibody to decrease. Because of this, this diagnostic agent can achieve an effect of diagnosing the above diseases.

Examples of a detection method at the time of using the antibody as a diagnostic agent can herein include, but are not limited to, a radioimmunoassay, an enzyme immunoassay, a fluoroimmunoassay, a luminescence immunoassay, immunoprecipitation, immune nephelometry, and the like. The enzyme immunoassay is preferable. Particularly preferred is an ELISA (e.g., a sandwich ELISA). The above immunological method such as an ELISA can be carried out using a procedure known to those skilled in the art. In addition, the diagnostic agent includes a reagent for PET (Positron Emission Tomography), or a reagent or material used for experiments.

For example, a typical detection method using the above anti-integrin α8β1 antibody can include: immobilizing the above anti-integrin α8β1 antibody on a support; adding a test sample thereto; incubating them; causing the above anti-integrin α8β1 antibody to bind to integrin α8β1, a recipient, in the test sample, and thereafter; washing them; detecting the integrin α8β1 binding to the support via the above anti-integrin α8β1 antibody, thereby detecting the integrin α8β1 in the test sample.

Examples of a preferable embodiment of detection of integrin α8β1, a recipient, binding to a support via the above anti-integrin α8β1 antibody can include a method using a labeled-substance-labeled anti-integrin α8β1 antibody. For example, a test sample is made to contact the above anti-integrin α8β1 antibody immobilized on a support. After washing, a labeled-substance-labeled anti-integrin α8β1 antibody is made to contact the test sample. Then, the labeled substance is detected using another labeled antibody to create an index for the integrin α8β1.

The labeling of the above anti-integrin α8β1 antibody can be performed using a commonly known procedure. Examples of the labeled substance which can be used include labeled substances known to those skilled in the art, such as fluorescent dye, an enzyme, a coenzyme, a chemiluminescent substance, and a radioactive material. Specific examples of the labeled substance can include a radioisotope (e.g., $^{32}P$, $^{14}C$, $^{125}I$, $^{3}H$, $^{131}I$), fluorescein, rhodamine, dansyl chloride, umbelliferone, luciferase, peroxidase, alkaline phosphatase, β-galactosidase, β-glucosidase, horseradish peroxidase, glucoamylase, lysozyme, saccharide oxidase, microperoxidase, biotin, and the like. When the biotin is used as a labeled substance, a biotin-labeled antibody is added. Then, avidin which is conjugated to an enzyme such as alkaline phosphatase is then further added.

Another embodiment of the present invention provides a reagent comprising the above anti-integrin α8β1 antibody or a reagent comprising an inhibitor of binding between integrin α8β1 and its ligand, the inhibitor containing the above anti-integrin α8β1 antibody. As used herein, the reagent contains a material, etc., for basic research, and can be used for, for example, an ELISA, Western blotting, or FACS analysis. Applications of this reagent can be used for, but are not particularly limited to, measurements of an expression level of integrin α8β1 in a living tissue. In addition, the applications may come with an instruction which describes usage and examples at the time of using the reagent, a document indicating where the instruction can be obtained, and/or various buffers.

As used herein, the term "cross-reactivity" generally refers to a characteristic in which a certain antibody has a significant binding affinity for any of two or more antigens having a similar structure. As used herein, the antigens having a similar structure include a protein having high homology.

Hereinafter, effects according to the above embodiments 1 and 2 will be further illustrated.

An embodiment of the present invention provides an anti-integrin α8β1 antibody which inhibits binding between integrin α8β1 and its ligand. When this anti-integrin α8β1 antibody is used, the binding between integrin α8β1 and its ligand can be inhibited. In addition, various functions such as integrin α8β1-mediated signal transduction can also be inhibited. Furthermore, a therapeutic or diagnostic agent for diseases involving integrin α8β1 can be obtained.

The above ligand may be osteopontin, fibronectin, tenascin, or vitronectin. In this case, when use of the above anti-integrin α8β1 antibody inhibits the above binding between integrin α8β1 and its ligand, various functions such as signal transduction involving the binding between integrin α8β1 and osteopontin, etc., can be inhibited. In addition, a therapeutic or diagnostic agent for diseases involving the binding between integrin α8β1 and osteopontin, etc., can be obtained.

In addition, the above ligand may be osteopontin. In this case, when use of the above anti-integrin α8β1 antibody inhibits the above binding between integrin α8β1 and its ligand, various functions can be inhibited which relate to signal transduction involving binding between integrin α8β1 and osteopontin (this binding has a particular importance during development of a therapeutic agent etc). In addition, a therapeutic or diagnostic agent for diseases involving the binding between integrin α8β1 and osteopontin can be obtained.

In addition, the above anti-integrin α8β1 antibodies may include an anti-integrin α8β1 antibody which also binds to integrin α8β1 derived from mammals of different species. In this case, use of the above anti-integrin α8β1 antibody can inhibit various functions such as integrin α8β1-mediated signal transduction in mammals. In addition, a therapeutic or diagnostic agent for mammalian diseases involving integrin α8β1 can be obtained. In addition, the above anti-integrin α8β1 antibody can be suitably used as a component of an agent (e.g., a therapeutic agent) which is important to examine its effect on multiple organisms.

Also, the above anti-integrin α8β1 antibodies may include an anti-integrin α8β1 antibody which binds to integrin α8β1 derived from any of a human and a mouse. In this case, when the above anti-integrin α8β1 antibody is used, a therapeutic or diagnostic agent containing the above anti-integrin α8β1 antibody can be used for a human and a mouse. In addition, in order to acquire basic information on human application, a model mouse can be used.

In addition, the above anti-integrin α8β1 antibody may be an antibody which binds to an integrin α8 chain. The integrin α8 chain forms a heterodimer only with a β1 chain. Thus, the above anti-integrin α8 antibody can bind to integrin α8β1. Then, use of the above anti-integrin α8β1 antibody can inhibit the binding between integrin α8β1 and its ligand.

In addition, the above anti-integrin α8β1 antibody may be a monoclonal antibody. In this case, the above anti-integrin α8β1 antibody can recognize integrin α8β1 with high specificity, thereby efficiently binding to integrin α8β1. Also, the binding between integrin α8β1 and its ligand can be efficiently inhibited.

In addition, the above anti-integrin α8β1 antibodies may include one or more anti-integrin α8β1 antibodies selected from the group consisting of chicken antibodies, chimeric antibodies, humanized antibodies, and human antibodies. In this case, the above anti-integrin α8β1 antibodies contain a humanized amino acid sequence. When the antibody is used as a therapeutic agent, immunogenicity against a human can be decreased.

In addition, the above anti-integrin α8β1 antibodies may bind to wild type or mutant integrin α8β1. In this case, the above anti-integrin α8β1 antibodies can bind to integrin α8β1 having an amino acid sequence different from that of the wild type. Also, it is possible to inhibit the binding between integrin α8β1 having an amino acid sequence different from that of the wild type and its ligand.

In addition, the above anti-integrin α8β1 antibodies may be an antibody fragment. In this case, the above anti-integrin α8β1 antibodies are shorter than an entire antibody, so that their in vivo administration decreases immunogenicity. Also, the in vivo administration can increase their stability, or an effect of increasing an antibody production efficiency, etc., can be achieved. Additionally, this antibody fragment contains a functional portion of the above anti-integrin α8β1 antibodies. For example, the antibody fragment may comprise heavy chain CDR1 to CDR3, or light chain CDR1 to CDR3.

Another embodiment of the present invention provides a polynucleotide comprising a nucleotide sequence encoding the above anti-integrin α8β1 antibody. In this case, when the above polynucleotide is used, the above anti-integrin α8β1 antibody can be produced by using a procedure known in the art.

Another embodiment of the present invention provides a vector comprising the above polynucleotide or a portion thereof. In this case, when the above vector is used, the above anti-integrin α8β1 antibody can be produced by using a procedure known in the art.

Another embodiment of the present invention provides an inhibitor of binding between integrin α8β1 and its ligand, the inhibitor comprising the above anti-integrin α8β1 antibody. If this inhibitor of binding between integrin α8β1 and its ligand is used, various functions such as integrin α8β1-mediated signal transduction can be inhibited. Also, a therapeutic or diagnostic agent for diseases involving integrin α8β1 can be obtained.

Another embodiment of the present invention provides a therapeutic agent comprising the above anti-integrin α8β1 antibody, wherein the agent is used for one or more diseases selected from the group consisting of cancer, arthritis, glaucoma, and neuropathic pain. When this therapeutic agent is used, an effect of treating the above diseases can be achieved.

In addition, this therapeutic agent may be a therapeutic agent for the above diseases in mammals. In this case, when the above therapeutic agent is used, an effect of treating the above diseases in mammals can be obtained.

Another embodiment of the present invention provides a diagnostic agent comprising the above anti-integrin α8β1 antibody, wherein the diagnostic agent is used for one or more diseases selected from the group consisting of pulmonary fibrosis, hepatic fibrosis, renal failure, inner ear disease, tumor, arthritis, glaucoma, and neuropathic pain. In this case, use of the above anti-integrin α8β1 antibody can achieve an effect of diagnosing the above diseases.

In addition, this diagnostic agent may be a diagnostic agent for the above diseases in mammals. In this case, use of the above diagnostic agent can achieve an effect of diagnosing the above diseases in mammals.

Another embodiment of the present invention provides a reagent comprising the above anti-integrin α8β1 antibody. In this case, use of the above reagent allows for application to experiments (e.g., an ELISA) involving integrin α8β1, investigation of the localization of integrin α8β1 in mammalian tissues or cells, or the like.

Another embodiment of the present invention provides an anti-integrin α8β1 antibody which binds to integrin α8β1 derived from mammals of different species. When this anti-integrin α8β1 antibody is used, it is possible to examine the localization of integrin α8β1 in mammalian tissues or cells etc. In addition, when used as a therapeutic or diagnostic agent comprising the above anti-integrin α8β1 antibody, the above anti-integrin α8β1 antibodies can be used for mammals of different species.

In addition, these anti-integrin α8β1 antibodies may include an anti-integrin α8β1 antibody which binds to integrin α8β1 derived from any of a human and a mouse. In this case, when the anti-integrin α8β1 antibodies are used, it is possible to examine the localization of integrin α8β1 in tissues or cells affected by human and mouse diseases. In addition, when used as a therapeutic or diagnostic agent comprising the above anti-integrin α8β1 antibody, the above anti-integrin α8β1 antibodies can be used for a human and a mouse. In addition, in order to acquire basic information on human application, a model mouse can be used.

In addition, these anti-integrin α8β1 antibodies may include an antibody which binds to an integrin α8 chain. The integrin α8 chain forms a heterodimer only with a β1 chain. Consequently, the above anti-integrin α8 antibody can bind to integrin α8β1. Because of this, when the above anti-integrin α8β1 antibody is used, it is possible to examine the localization of an integrin α8 chain and integrin α8β1 in mammalian tissues or cells etc. In addition, when the above anti-integrin α8β1 antibodies are used as a therapeutic or diagnostic agent comprising the above anti-integrin α8β1 antibody, integrin α8β1 can be used as their target.

In addition, this anti-integrin α8β1 antibody may be a monoclonal antibody. In this case, the above anti-integrin α8β1 antibody can recognize integrin α8β1 with high specificity, thereby efficiently binding to integrin α8β1. In addition, when this anti-integrin α8β1 antibody is used to inhibit the binding between integrin α8β1 and its ligand, its inhibition efficiency increases.

Another embodiment of the present invention provides a polynucleotide comprising a nucleotide sequence encoding an anti-integrin α8β1 antibody which binds to integrin α8β1 derived from mammals of different species. In this case, when this polynucleotide is used, the above anti-integrin α8β1 antibody can be produced by using a procedure known in the art.

Another embodiment of the present invention provides a vector comprising a polynucleotide or a portion thereof, the polynucleotide containing a nucleotide sequence encoding an anti-integrin α8β1 antibody which binds to integrin α8β1 derived from mammals of different species. In this case, when the above vector is used, the above anti-integrin α8β1 antibody can be produced by using a procedure known in the art.

Another embodiment of the present invention provides an inhibitor of binding between integrin α8β1 and its ligand, the inhibitor comprising an anti-integrin α8β1 antibody which binds to integrin α8β1 derived from mammals of different species. If this inhibitor of binding between integrin α8β1 and its ligand is used, various functions such as integrin α8β1-mediated signal transduction can be inhibited. Also, a therapeutic or diagnostic agent for diseases involving integrin α8β1 can be obtained.

Another embodiment of the present invention provides a therapeutic agent comprising an anti-integrin α8β1 antibody which binds to integrin α8β1 derived from mammals of different species, wherein the therapeutic agent is used for one or more diseases selected from the group consisting of cancer, arthritis, glaucoma, and neuropathic pain. When this therapeutic agent is used, an effect of treating the above diseases can be achieved.

In addition, this therapeutic agent may be a therapeutic agent for the above diseases in mammals. In this case, when the above therapeutic agent is used, an effect of treating the above diseases in mammals can be obtained.

Another embodiment of the present invention provides a diagnostic agent comprising an anti-integrin α8β1 antibody which binds to integrin α8β1 derived from mammals of different species, wherein the diagnostic agent is used for one or more diseases selected from the group consisting of pulmonary fibrosis, hepatic fibrosis, renal failure, inner ear disease, tumor, arthritis, glaucoma, and neuropathic pain. In this case, use of the above anti-integrin α8β1 antibody can achieve an effect of diagnosing the above diseases.

In addition, this diagnostic agent may be a diagnostic agent for the above diseases in mammals. In this case, use of the above diagnostic agent can achieve an effect of diagnosing the above diseases in mammals.

Another embodiment of the present invention provides a reagent comprising an anti-integrin α8β1 antibody which binds to integrin α8β1 derived from mammals of different species. In this case, use of the above reagent allows for application to experiments (e.g., an ELISA) involving integrin α8β1, investigation of the localization of integrin α8β1 in mammalian tissues or cells, or the like.

Another embodiment of the present invention provides a process for producing an anti-integrin α8β1 antibody, the process comprising the step of immunizing a chicken with an antigen containing an integrin α8 chain. If this production process is used, it is possible to obtain an anti-integrin α8β1 antibody which inhibits binding between integrin α8β1 and its ligand or an anti-integrin α8β1 antibody which binds to integrin α8β1 derived from mammals of different species. In addition, it is possible to obtain an inhibitor of binding between, integrin α8β1 and its ligand, the inhibitor comprising an anti-integrin α8β1 antibody.

As described above, embodiments of the present invention has been illustrated. These embodiments are examples of the present invention. Accordingly, combinations of the above embodiments or various configurations other than the above embodiments can be adopted.

EXAMPLES

Hereinafter, the present invention is further illustrated by referring to Examples. The present invention, however, is not limited to them.

Example 1

Production of Mouse Integrin α8-Expressing Chicken Cell Line and Immunization of Chicken Therewith The cDNA of a mouse integrin α8 chain was cloned into a mammalian expression vector. Next, the expression vector was transfected into a chicken lymphoblastoid cell line by electroporation. Then, an antibiotic was added, and vector-expressing cells were selected. A chicken was hyperimmunized with the resulting mouse integrin α8-expressing cells. The antibody titer was determined by flow cytometry (FACS) analysis. The FACS analysis was performed in accordance with a typical protocol of FACSCalibur (BD, USA). It is known that an integrin α8 chain forms a heterodimer with a β1 chain (Luo et al., Annu Rev Immunol., 2007, 25, 619-47). In the above integrin α8-expressing cells, the α8 chain seemed to form a heterodimer with the β1 chain. Accordingly, an antibody as obtained by immunizing a chicken with the mouse integrin α8-expressing cells recognizes integrin α8β1, and can be used as an anti-integrin α8β1 antibody.

Example 2

Production of scFv Phage Antibody Library Prepared from Spleen of Immunized Chicken After a spleen was removed from an immunized chicken, lymphocytes were separated. RNA was extracted from the resulting lymphocytes. Then, cDNA was synthesized and an scFv phage antibody library was produced. Production of the phage antibody library was carried out in accordance with a typical procedure described in Nakamura et al., J Vet Med Sci., 2004, July, 66(7), 807-14.

Example 3

Panning Selection

The scFv phage library was added to mouse integrin α8 expression-free cells, and non-specific phages were adsorbed. Next, the resulting library was reacted with the mouse integrin α8-expressing cells. The mixture was washed with an organic solvent. Then, phages which had bound to the mouse integrin α8-expressing cells were collected, and *Escherichia coli* bacteria were infected therewith. After panning was performed four times, the library reactivity was examined by FACS analysis using the mouse integrin α8-expressing cells. Since the third library had high reactivity, cloning of phages was carried out from the third library. After selection of positive clones, their sequences were determined. The cell panning was performed according to a procedure described in Giordano et al., Nat Med., 2001, November, 7(11), 1249-53.

Example 4

Selection of Clones Cross-Reacted with Human Integrin α8 Chain

In order to obtain an antibody which was cross-reacted with a human integrin α8 chain, a human integrin α8-expressing chicken lymphoblastoid cell line was produced. Clones which had been cross-reacted with the human integrin α8-expressing cell line were selected by FACS.

Example 5

Engineering of Recombinant IgY (rIgY) Antibody and Evaluation of its Cross-Reactivity (5-1) Engineering of Recombinant IgY (rIgY) Antibody By using a gene encoding an scFv phage antibody as a template, chicken antibody genes of $V_H$ and $V_L$ were amplified by PCR. Next, the overlap PCR of a leader sequence and a constant region of the chicken antibody gene was carried out, and they were cloned into an rIgY-expressing vector. Then, the prepared H-chain and L-chain constructs were transfected into mammalian cultured cells. After that, an expressed antibody protein was purified. Engineering of the rIgY antibody was performed in accordance with a typical procedure described in Shimamoto et al., Biologicals, 2005, September, 33(3), 169-74.

(5-2) Evaluation of Cross-Reactivity Toward Human and Mouse Integrin α8β1

Figure 4:
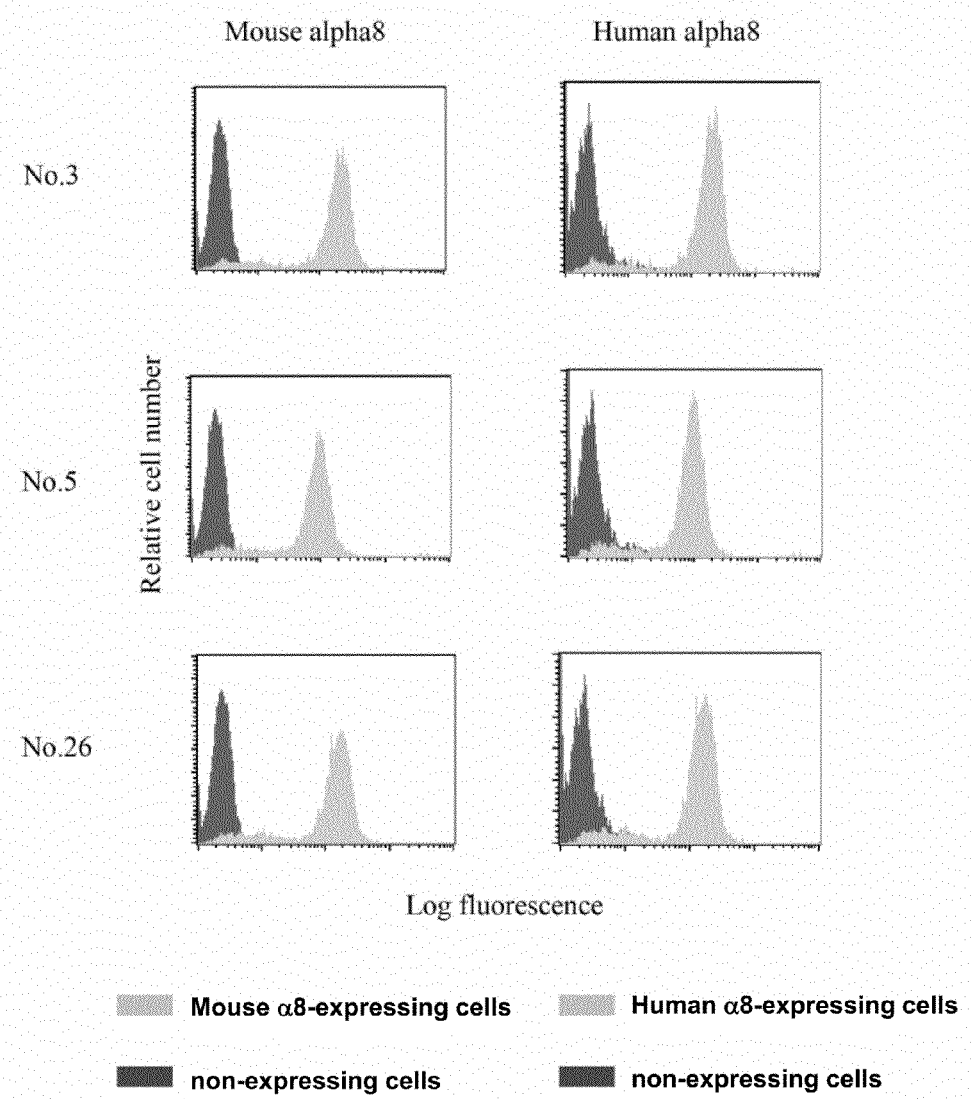
FIG. 4 is graphs showing results of investigating cross-reactivity of anti-integrin α8β1 chicken monoclonal antibodies toward human and mouse integrin α8β1 by FACS analysis.

Three kinds (No. 3, No. 5, and No. 26) of the anti-integrin α8β1 chicken monoclonal antibody as obtained in the above experiments were used to investigate their cross-reactivity toward a human integrin α8-expressing cell line and a mouse integrin α8-expressing cell line by FACS analysis. FIG. 4 shows the results. The peak positions of the three kinds of the anti-integrin α8β1 chicken monoclonal antibody were clearly shifted to the right side, compared with those observed at the time of using non-expressing cells. This demonstrates that those antibodies can bind to integrin α8β1 derived from both a human and a mouse.

Respective plasmids containing a DNA sequence encoding a heavy chain of the anti-integrin α8β1 chicken monoclonal antibodies (No. 3, No. 5 or No. 26) were domestically deposited at Biological Resource Center, National Institute of Technology and Evaluation (Kazusa Kamatari 2-5-8, Kisarazu-city, Chiba) on Oct. 16, 2009. After that, the above domestically deposited plasmids were changed to international deposition as Accession No: NITE BP-824, Accession No: NITE BP-826, and Accession No: NITE BP-828, respectively, under the Budapest Treaty on Oct. 12, 2010.

Respective plasmids containing a DNA sequence encoding a light chain of the anti-integrin α8β1 chicken monoclonal antibodies (No. 3, No. 5 or No. 26) were domestically deposited at Biological Resource Center, National Institute of Technology and Evaluation on Oct. 16, 2009. After that, the above domestically deposited plasmids were changed to international deposition as Accession No: NITE BP-825, Accession No: NITE BP-827, and Accession No: NITE BP-829, respectively, under the Budapest Treaty on Oct. 12, 2010. It is notable that those six deposited plasmids were constructed using the same expression vector as in the above (5-1).

In addition, amino acid sequences of the heavy chain CDRs and the light chain CDRs of the above anti-integrin α8β1 chicken monoclonal antibodies (No. 3, No. 5, and No. 26) were examined. Table 1 shows the results. In Table 1, the "X" denotes an amino acid which was unable to be analyzed by amino acid analysis.

TABLE 1

|  |  |  | SEQ ID NO: |
|---|---|---|---|
| ■No. 3 |  | Heavy Chain |  |
|  | CDR1 | SYDMV | 1 |
|  | CDR2 | IYSAGSGPQYAPAVKG | 2 |
|  | CDR3 | ADSTYCASGSCYAADSID | 3 |
| ■No. 3 |  | Light Chain |  |
|  | CDR1 | SGGGSWYG | 10 |
|  | CDR2 | DNTNRPS | 11 |
|  | CDR3 | GSADSTDAV | 12 |
| ■No. 5 |  | Heavy Chain |  |
|  | CDR1 | SYDMA | 4 |
|  | CDR2 | IDDDDSFTLYGAAVKG | 5 |
|  | CDR3 | VGDGYCGWSACGGSID | 6 |
| ■No. 5 |  | Light Chain |  |
|  | CDR1 | SGDESYYG | 13 |
|  | CDR2 | SNDKRPS | 14 |
|  | CDR3 | GXYDSSTYAGI | 15 |
| ■No. 26 |  | Heavy Chain |  |
|  | CDR1 | GHDMA | 7 |
|  | CDR2 | IGSSGSNTNYGTAVKG | 8 |
|  | CDR3 | PGSCYGCTPDAGEID | 9 |
| ■No. 26 |  | Light Chain |  |
|  | CDR1 | SGSSGSYYG | 16 |
|  | CDR2 | ESTKRPS | 17 |
|  | CDR3 | GNEDSSYVGI | 18 |

(5-3) Discussion of the Results

Anti-integrin α8β1 antibodies which bound to integrin α8β1 derived from any of a human and a mouse were obtained. Use of these antibodies enables the localization of integrin α8β1 to be investigated in normal and disease-related tissues or cells, etc., in a human. Further, the present antibody cross-reacts with mouse integrin α8β1, so that the localization of integrin α8β1 can be investigated in a model mouse. Accordingly, the present antibody can be suitably used as a material to acquire basic information on application to a human.

Example 6

Figure 5:
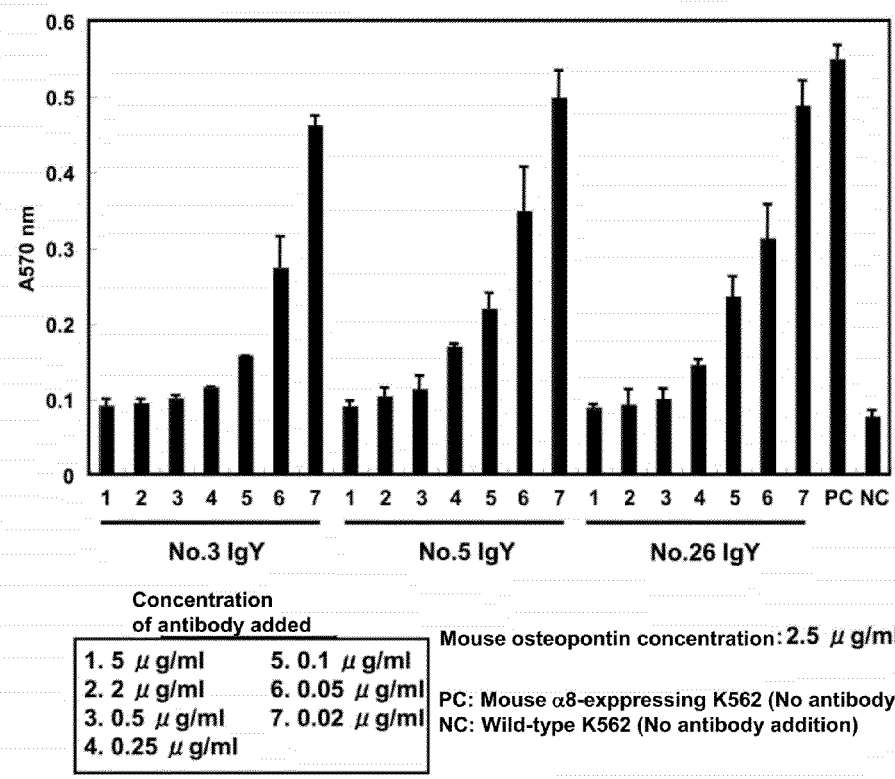
FIG. 5 is a graph showing results of investigating activities of inhibiting binding between integrin α8-expressing K562 cells and mouse osteopontin by anti-integrin α8β1 chicken monoclonal antibodies.

Evaluation of Activity of Inhibiting Binding to Ligand (6-1) Measurement of Activity of Inhibiting Binding to Ligand Mouse osteopontin (2.5 μg/ml) was immobilized on a 96-well plate, and integrin α8-expressing K562 cells were added thereto at 1×10E5 cells/well. The above No. 3, No. 5, or No. 26 antibody was also added at the concentration designated in FIG. 5, and it was examined how much the antibody inhibited adhesion of cells to osteopontin. In FIG. 5, the adhering cells were detected at A570 nm. The results indicate that the lower a value at A570 nm, the less the binding between the integrin α8-expressing K562 cells and osteopontin.

Adhesion of the positive control (PC) was set to 100. When the No. 3 antibody was added at 0.05 μg/ml, and the No. 5 antibody and the No. 26 antibody were added at 0.1 μg/ml, the results showed that the respective antibodies were found to exhibit an inhibitory activity of 50%.

(6-2) Discussion of the Results

The anti-integrin α8β1 chicken monoclonal antibodies had a remarkable activity of inhibiting the binding between osteopontin and integrin α8β1. This suggests that the above antibodies can be an extremely effective material as a therapeutic agent for various diseases involving the interaction between osteopontin and integrin α8β1. In addition, it can be understood in light of common technical knowledge in the art that the above antibodies exert a similar effect on a ligand (e.g., fibronectin, tenascin, or vitronectin) other than osteopontin and can inhibit the binding to integrin α8β1.

Example 7

Experiments Comparing Chicken-Derived Anti-Integrin α8β1 Antibodies and Mouse-Derived Anti-Integrin α8β1 Antibodies (7-1) FACS Analysis FACS analysis was carried out in the following procedure with the above No. 3 anti-integrin α8β1 chicken monoclonal antibody (hereinafter, sometimes referred to as "No. 3 chicken IgY"), an anti-integrin α8β1 chicken-mouse chimeric antibody (hereinafter, sometimes referred to as "No. 3 chicken-mouse chimeric IgG") which is a recombinant antibody derived from the above antibody, and two kinds of an anti-integrin α8β1 mouse monoclonal antibody (7A5 and 10A8). Then, their reactivity was compared. Of note is that 7A5 and 10A8 are antibodies described in a publication (Sato et al., J Biol Chem., 2009, May 22, 284(21), 14524-36, Epub Apr. 2, 2009), and have been provided from the authors in this research article. Those 7A5 and 10A8 are antibodies which have been produced by immunizing a mouse with a recombinant soluble integrin α8β1 as an antigen.

Each of the above four kinds of the test antibodies, as a primary antibody, was reacted at a concentration of 1 μg/ml with integrin α8β1-expressing SW480 cells (at 4° C., for 30 min). After washing of the cells, an FITC-labeled secondary antibody was added and the mixture was reacted at 4° C. for 30 minutes. After additional washing, FACS analysis was carried out. As a control, integrin α8β1 expression-free cells were used.

Figure 6:
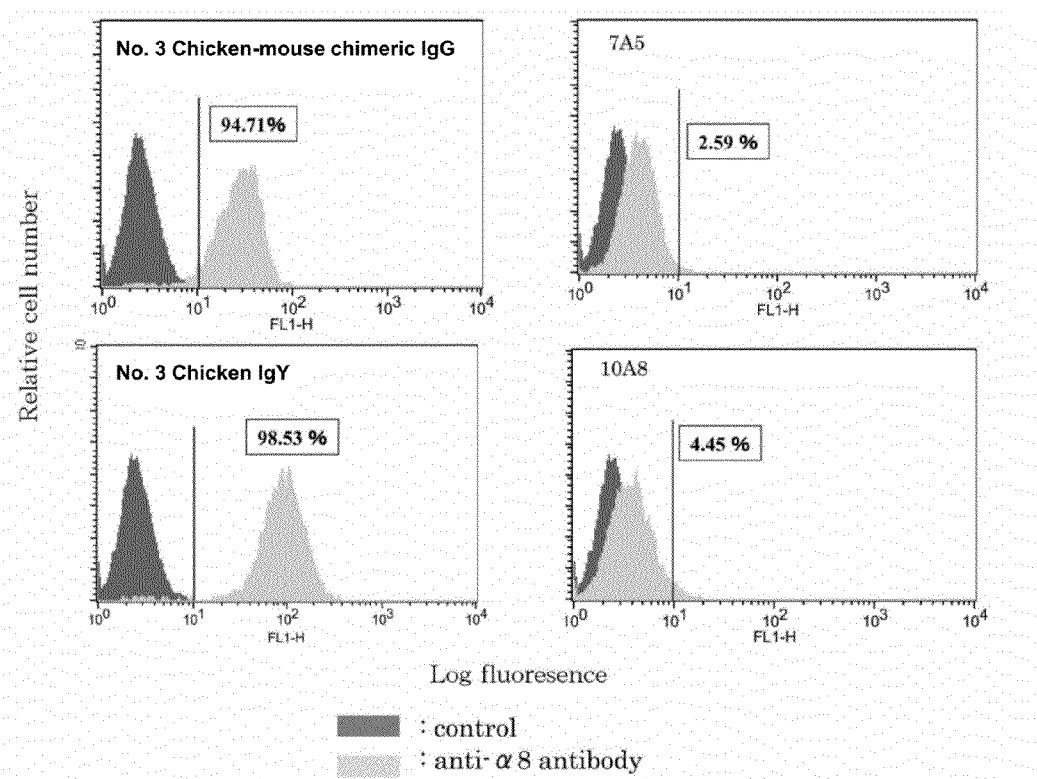
FIG. 6 is graphs showing results of investigating reactivity of chicken-derived anti-integrin α8β1 antibodies and mouse-derived anti-integrin α8β1 antibodies toward integrin α8β1-expressing SW480 cells by FACS analysis.

FIG. 6 shows the results. The No. 3 chicken IgY and the No. 3 chicken-mouse chimeric IgG had a large right shift, and were strongly positive for integrin α8β1 (No. 3 chicken IgY: 94.71% positive; No. 3 chicken-mouse chimeric IgG: 98.53% positive). In contrast, two kinds of the integrin α8β1 mouse monoclonal antibody were weakly positive (7A5: 2.59% positive; 10A8: 4.45% positive).

(7-2) Cell Adhesion Assay

With regard to an activity of inhibiting adhesion between integrin α8β1 and osteopontin, the above four kinds of the antibodies (No. 3 chicken IgY, No. 3 chicken-mouse chimeric IgG, 7A5, 10A8) were examined according to the following procedure. First, each of the above four kinds of the antibodies were reacted at a concentration of 5 μg/ml with the integrin α8β1-expressing SW480 cells for 30 minutes. The cell-containing solution after the reaction was added to a plate on which mouse osteopontin (50 μg/ml) had been immobilized. Next, the solution was cultured for 45 minutes. Then, the cells were washed, fixed, and stained. The fixed and stained cells were lysed with Triton X-100. After that, absorbance at 570 nm was examined. In addition, in a similar procedure, absorbance was determined in the case of using SW480 cells which neither have the antibody nor express integrin α8β1 (hereinafter, sometimes referred to as "a SW480 no-antibody-addition group").

Figure 7:
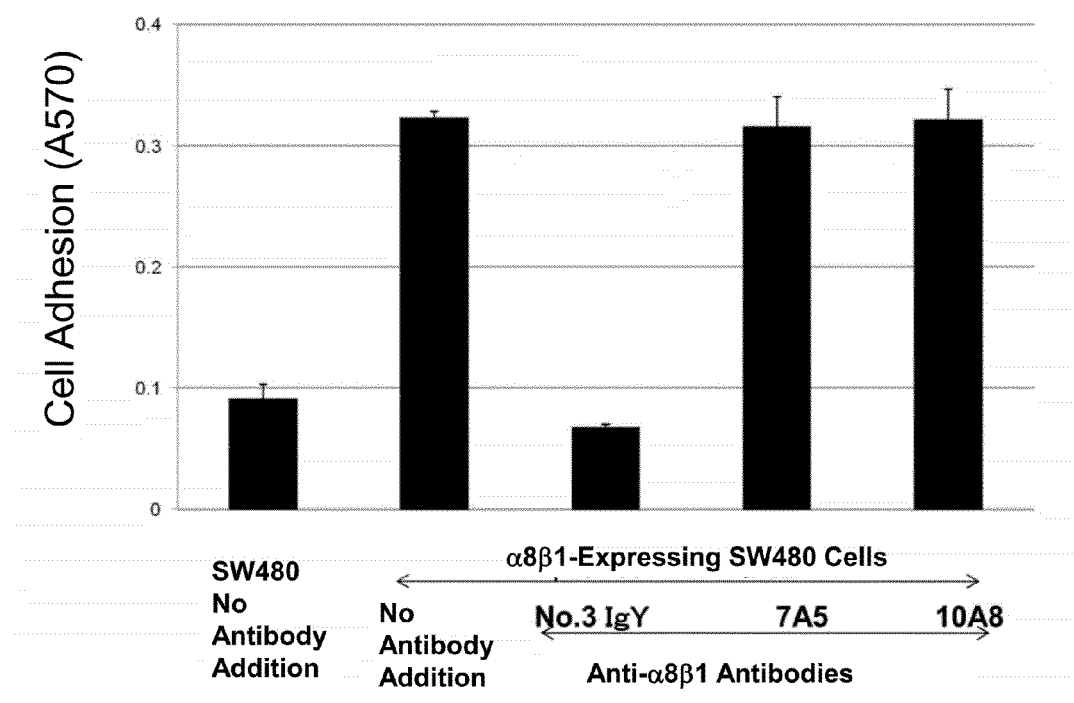
FIG. 7 is a graph showing results of investigating activities of inhibiting binding between integrin α8β1 and its ligand by a chicken-derived anti-integrin α8β1 antibody and mouse-derived anti-integrin α8β1 antibodies.

FIG. 7 shows the results. An activity of inhibiting cell adhesion was observed for the No. 3 chicken IgY, but not for 7A5 and 10A8. The degree of cell adhesion of the No. 3 chicken IgY-addition group was lower than that of the SW480 no-antibody-addition group. Hence, the rate of inhibiting the cell adhesion by the No. 3 chicken IgY was considered to be 100%. In contrast, there was almost no difference regarding the 7A5-addition group and the 10A8-addition group in the degree of cell adhesion, compared with a group in which integrin α8β1-expressing SW480 cells had not been treated with antibody. Thus, 7A5 and 10A8 can be considered to exert no activity of inhibiting the cell adhesion.

(7-3) Discussion of the Results

The above comparative experiments have demonstrated that the anti-integrin α8β1 antibodies as obtained in the Examples of the present application are remarkably superior in the aspects of both the activity of binding to integrin α8β1 and the activity of inhibiting the binding between integrin α8β1 and osteopontin, compared with the known conventional anti-integrin α8β1 antibodies. In addition, in the Examples of the present application, a production process having characteristic features has been adopted, including immunization using a chicken, use of the integrin α8-expressing cell line as an antigen, cell panning using the integrin α8-expressing cell line, and the like.

<Discussion of the Results>

In the above Examples 1 to 7, anti-integrin α8β1 antibodies were obtained which 1) bound to integrin α8β1 derived from both a human and a mouse, 2) had a high activity of binding to integrin α8β1, and 3) inhibited binding of osteopontin to integrin α8β1. These characteristics indicate that the resulting antibodies can be an industrially excellent material for a therapeutic agent, a diagnostic agent, a reagent, or the like. In addition, the integrin α8β1 is not limited to a human-derived one, but may include a mouse-derived one. Accordingly, it can be suitably used for research using a model mouse and treatment thereof. Many mouse strains have a known genetic background, have a property of a short generation time, and further are particularly important organisms used for development of a therapeutic or diagnostic agent because mice are susceptible to diseases similar to those of a human.

Here, it is described that integrin α8β1 activates PI3K (Hynes R O., Cell, 2002, Sep. 20, 110(6), 673-87; and Farias et al., Biochem Biophys Res Commun., 2005, Apr. 1, 329(1), 305-11). The PI3K is a kinase which phosphorylates the 3rd position of an inositol ring of inositol phospholipid, a component of a membrane. The PI3K is known to be involved in various diseases. For example, it is described that the inhibition of PI3K functions by an antagonist exerts an in vivo therapeutic effect on an animal model for cancer (Yaguchi et al., J Natl Cancer Inst., 2006, Apr. 19, 98(8), 545-56). Also, it is described that a therapeutic effect has been exerted in vivo on an animal model for non-small cell lung carcinoma (Boehle et al., Langenbecks Arch Surg., 2002, October, 387(5-6), 234-9 (Epub, Sep. 28, 2002)), arthritis (Tamura et al., Jpn J Clin Immunol., 2007, 30(5), 369-374), neuropathic pain (JP2007-63205A), or glaucoma (JP2003-104909A).

In addition, it is described that integrin α8β1 activates FAK (Richard et al., Cell, Vol. 110, 673-687, Sep. 20, 2002; Shouchun Liu, Journal of Cell Science, 113, 3563-3571 (2000); and Littlewood et al., Nat Genet., 2000, April, 24(4), 424-8). The FAK is an intracellular tyrosine kinase whose activated form interacts with many signaling molecules such as a Src-family kinase and a phosphatidylinositol 3-kinase. The FAK is known to be involved in various diseases. For example, it has been described that the inhibition of FAK functions by an antagonist exerts an in vivo therapeutic effect on an animal model for pancreatic cancer (Hatakeyama et al., Journal of Clinical Oncology, Vol. 24, No 18S (June 20, Supplement), 2006, 13162) or glioma (Liu et al., Mol Cancer Ther., 2007, April, 6(4), 1357-67).

Accordingly, the antibodies as obtained in Examples 1 to 7 may inhibit the PI3K-FAK signal transduction, which is mediated through integrin α8β1 from osteopontin. Thus, the antibodies seem to exert a remarkable therapeutic effect on the above diseases (i.e., cancer, arthritis, glaucoma, or neuropathic pain).

In addition, when the antibodies are used as a diagnostic agent, it seems to be possible to diagnose the above diseases by examining and comparing the modes of binding of the antibodies to integrin α8β1 in, for example, cells, blood, serum, body fluid, or pathologic sections in any of the above diseases. For example, the excessive activation of PI3K or FAK is responsible for the diseases, and the activation may be caused by high expression of integrin α8β1. In that case, the binding level of the anti-integrin α8β1 antibodies as obtained in Examples 1 to 7 increases. In addition, the excessive activation of PI3K or FAK may be caused by high expression of osteopontin. In that case, due to competition with its ligand, the above binding level of the anti-integrin α8β1 antibodies seems to decrease.

Further, it is described that kidney morphogenesis failure (Muller et al., Cell. 1997 Mar. 7; 88(5):603-13.) and inner hair cell deficiency (Littlewood et al., Nat Genet., 2000, April, 24(4), 424-8) occur in an integrin α8-knockout mouse. Furthermore, it is described that its high expression is observed in pulmonary fibrosis or hepatic fibrosis (Levine et al., Am J Pathol., 2000, June, 156(6), 1927-35). Consequently, the antibodies as obtained in Examples 1 to 7 can be used as a probe to investigate an expression level of an integrin α8 chain in cells or tissues etc. Thus, the antibodies seem to be able to be suitably used as a diagnostic agent for renal failure caused by kidney morphogenesis failure, inner ear disease caused by inner hair cell deficiency, pulmonary fibrosis, or hepatic fibrosis. For example, when the high expression of integrin α8β1 is responsible for the diseases, the binding level of the anti-integrin α8β1 antibodies increases. When the high expression of osteopontin is responsible for the diseases, the competition with osteopontin seems to decrease the binding level of the anti-integrin α8β1 antibodies. Also, the antibodies seem to be able to be suitably used as a prenatal diagnostic agent for kidney morphogenesis failure or inner hair cell-deficiency.

In addition, the antibodies as obtained in Examples 1 to 7 seem to be an extremely effective material for a reagent used in integrin α8β1-related basic research or regenerative medicine etc.

It is notable that regardless of the presence of an antibody binding to integrin α8β1, an antibody capable of inhibiting the binding to its ligand has not been obtained. This fact suggests possibilities that a region involving the binding between integrin α8β1 and its ligand has a structure which is unlikely to be affected by the antibody, and that a region involving the binding between integrin α8β1 and its ligand is unlikely to become an epitope. Obtaining an antibody which inhibits the binding between integrin α8β1 and its ligand has also been considered uneasy. However, the results as obtained in Examples of the present application have reversed the concerned matter.

As described above, the present invention has been described based on Examples. These Examples are absolutely examples. It should be understood by those skilled in the art that various modifications are possible, and those modifications are also within the scope of the present invention.

The invention claimed is:

1. An anti-integrin α8β1 antibody selected from the group consisting of:
   a) an anti-integrin α8β1 antibody comprising: heavy chain CDR1 having the amino acid sequence set forth in SEQ ID No: 1; heavy chain CDR2 having the amino acid sequence set forth in SEQ ID No: 2; heavy chain CDR3 having the amino acid sequence set forth in SEQ ID No: 3; light chain CDR1 having the amino acid sequence set forth in SEQ ID No: 10; light chain having the amino acid sequence set forth in SEQ ID No: 11; and light chain CDR3 having the amino acid sequence set forth in SEQ ID No: 12;
   b) an anti-integrin α8β1 antibody comprising: heavy chain CDR1 having the amino acid sequence set forth in SEQ ID No: 4; heavy chain CDR2 having the amino acid sequence set forth in SEQ ID No: 5; heavy chain CDR3 having the amino acid sequence set forth in SEQ ID No: 6; light chain CDR1 having the amino acid sequence set forth in SEQ ID No: 13; light chain CDR2 having the amino acid sequence set forth in SEQ ID No: 14; and light chain CDR3 having the amino acid sequence set forth in SEQ ID No: 15; and
   c) an anti-integrin α8β1 antibody comprising: heavy chain CDR1 having the amino acid sequence set forth in SEQ ID No: 7; heavy chain CDR2 having the amino acid sequence set forth in SEQ ID No: 8; heavy chain CDR3 having the amino acid sequence set forth in SEQ ID No: 9; light chain CDR1 having the amino acid sequence set forth in SEQ ID No: 16; light chain CDR2 having the amino acid sequence set forth in SEQ ID No: 17; and light chain CDR3 having the amino acid sequence set forth in SEQ ID No: 18;
   or an antigen-binding fragment thereof.

2. The anti-integrin α8β1 antibody, or the antigen-binding fragment thereof of claim 1, wherein the antibody or antibody fragment is obtained by using integrin α8-expressing cells as an antigen.

3. The anti-integrin α8β1 antibody, or the antigen-binding fragment thereof of claim 2, wherein the antibody or antibody fragment is obtained by a process for producing an antibody, comprising the steps of:
   introducing a polynucleotide encoding integrin α8 into cells;
   expressing integrin α8 in the cells; and
   immunizing a chicken with the antigen containing cells expressing the integrin α8 or a cell membrane having the integrin α8.

4. The anti-integrin α8β1 antibody, or the antigen-binding fragment thereof according to claim 1, wherein the antibody or antibody fragment inhibits binding between integrin α8β1 and osteopontin.

5. The anti-integrin α8β1 antibody, or the antigen-binding fragment thereof according to claim 4, wherein the antibody or antibody fragment binds to integrin α8β1 of any of a human and a mouse.

6. The anti-integrin α8β1 antibody, or the antigen-binding fragment thereof according to claim 2, wherein the antibody or antibody fragment inhibits binding between integrin α8β1 and osteopontin.

7. The anti-integrin α8β1 antibody, or the antigen-binding fragment thereof according to claim 1, wherein the antibody or antibody fragment binds to integrin α8β1 of any of a human and a mouse.

8. The anti-integrin α8β1 antibody, or the antigen-binding fragment thereof according to claim 1, wherein the antibody or antibody fragment is a monoclonal antibody or a fragment thereof, respectively.

* * * * *